United States Patent
Mothilal et al.

(10) Patent No.: US 12,426,811 B2
(45) Date of Patent: Sep. 30, 2025

(54) DETECTION OF CHANGES IN PATIENT HEALTH BASED ON GLUCOSE DATA

(71) Applicant: Medtronic, Inc., Minneapolis, MN (US)

(72) Inventors: Kamal Deep Mothilal, Maple Grove, MN (US); Michael D. Eggen, Chisago City, MN (US); Ning Yu, Columbia Heights, MN (US); John P Keane, Shoreview, MN (US); Shantanu Sarkar, Roseville, MN (US); Randal C. Schulhauser, Phoenix, AZ (US); David L. Probst, Chandler, AZ (US); Mark R. Boone, Gilbert, AZ (US); Kenneth A Timmerman, Robbinsdale, MN (US); Stanley J Taraszewski, Plymouth, MN (US); Matthew A Joyce, Maple Grove, MN (US); Amruta Paritosh Dixit, Maple Grove, MN (US); Kathryn E. Hilpisch, Cottage Grove, MN (US); Kathryn Ann Milbrandt, Ham Lake, MN (US); Laura M Zimmerman, Maple Grove, MN (US); Matthew L Plante, Danbury, WI (US)

(73) Assignee: Medtronic, Inc., Minneapolis, MN (US)

( * ) Notice: Subject to any disclaimer, the term of this patent is extended or adjusted under 35 U.S.C. 154(b) by 612 days.

(21) Appl. No.: 17/663,657

(22) Filed: May 16, 2022

(65) Prior Publication Data
US 2022/0369961 A1    Nov. 24, 2022

Related U.S. Application Data

(60) Provisional application No. 63/191,201, filed on May 20, 2021.

(51) Int. Cl.
 A61B 5/145    (2006.01)
 A61B 5/00     (2006.01)
 (Continued)

(52) U.S. Cl.
 CPC ........ *A61B 5/14532* (2013.01); *A61B 5/0205* (2013.01); *A61B 5/14503* (2013.01);
 (Continued)

(58) Field of Classification Search
 CPC .............. A61B 5/14532; A61B 5/0205; A61B 5/14503; A61B 5/7267; A61B 5/7275;
 (Continued)

(56) References Cited

U.S. PATENT DOCUMENTS

| | | |
|---|---|---|
| 9,629,548 B2 | 4/2017 | Sachanandani et al. |
| 10,172,568 B2 | 1/2019 | Sharma et al. |

(Continued)

FOREIGN PATENT DOCUMENTS

| | | |
|---|---|---|
| KR | 20190076237 A | 7/2019 |
| RU | 2707050 C1 | 11/2019 |

OTHER PUBLICATIONS

Helgason, "Blood Glucose and Stroke" (Year: 1988).*

(Continued)

*Primary Examiner* — Eric F Winakur
*Assistant Examiner* — Noah M Healy
(74) *Attorney, Agent, or Firm* — Shumaker & Sieffert, P.A.

(57) ABSTRACT

This disclosure is directed to systems and techniques for detecting change in patient health based upon patient data. In one example, a medical system comprising processing circuitry communicably coupled to a glucose sensor and configured to generate continuous glucose sensor measurements of a patient. The processing circuitry is further configured to: extract at least one feature from the continu- (Continued)

ous glucose sensor measurements over at least one time period, wherein the at least one feature comprises one or more of an amount of time within a pre-determined glucose level range, a number of hypoglycemia events, a number of hyperglycemia events, or one or more statistical metrics corresponding to the continuous glucose sensor measurements; apply a machine learning model to the at least one extracted feature to produce data indicative of a risk of a cardiovascular event; and generate output data based on the risk of the cardiovascular event.

24 Claims, 10 Drawing Sheets

(51) Int. Cl.
*A61B 5/0205* (2006.01)
*G16H 50/20* (2018.01)
*G16H 50/30* (2018.01)

(52) U.S. Cl.
CPC .......... *A61B 5/7267* (2013.01); *A61B 5/7275* (2013.01); *A61B 5/7282* (2013.01); *G16H 50/20* (2018.01); *G16H 50/30* (2018.01)

(58) Field of Classification Search
CPC . A61B 5/7282; A61B 5/0031; A61B 5/14552; A61B 5/14556; A61B 5/7264; G16H 50/30
See application file for complete search history.

(56) References Cited

U.S. PATENT DOCUMENTS

| | | | |
|---|---|---|---|
| 10,251,563 B2 | 4/2019 | Sweeney et al. | |
| 10,575,762 B2* | 3/2020 | Mayou | G16H 15/00 |
| 10,998,101 B1 | 5/2021 | Tran et al. | |
| 2015/0057512 A1 | 2/2015 | Kapoor | |
| 2019/0069851 A1 | 3/2019 | Sharma et al. | |
| 2019/0336076 A1 | 11/2019 | Kuhn et al. | |
| 2019/0357853 A1* | 11/2019 | Shi | A61B 5/742 |
| 2020/0187865 A1 | 6/2020 | Sharma et al. | |
| 2021/0020294 A1* | 1/2021 | Bharmi | G16H 50/30 |
| 2021/0290113 A1* | 9/2021 | Liu | G16H 10/40 |
| 2021/0391081 A1* | 12/2021 | Goldner | G16H 10/60 |
| 2024/0242834 A1* | 7/2024 | Deng | A61B 5/4839 |

OTHER PUBLICATIONS

Cowie et al., "Development and validation of an integrated diagnostic algorithm derived from parameters monitored in Implantable devices for identifying patients at risk for heart failure hospitalization in an ambulatory setting", European Heart Journal, European Society of Cardiology, Mar. 19, 2013, pp. 2472-2480.

Lawson et al., "Association Between Type 2 Diabetes and All-Cause Hospitalization and Mortality in the UK General Heart Failure Population", JACC: Heart Failure, vol. 6, No. 1, American College of Cardiology Foundation, Jan. 18, 2018, pp. 18-26.

Merchant et al., "Implantable Sensors for Heart Failure", Circ Arrhythm Electrophysiol, American Heart Association, Dec. 2010, pp. 657-667.

Atoui et al., "Cardiovascular risk stratification in decision support systems: A probabilistic approach. application to pHealth", 2006 Computers in Cardiology, IEEE, Sep. 2006, pp. 281-284.

Capes et al., "Stress hyperglycemia and increased risk of death after myocardial infarction in patients with and without diabetes: a systematic overview", the Lancet, vol. 355, No. 9206, Mar. 2000, pp. 773-778.

International Search Report and Written Opinion of International Application No. PCT/US2022/029602 dated Sep. 1, 2022, 13 pp.

The Decode Study Group et al., "Prediction of the risk of cardiovascular mortality using a score that includes glucose as a risk factor. The Decode Study", Diabetologia, vol. 47, No. 12, Dec. 2004, pp. 2118-2128.

* cited by examiner

DETECTION OF CHANGES IN PATIENT HEALTH BASED ON GLUCOSE DATA

This application claims the benefit of U.S. Provisional Application Ser. No. 63/191,201, filed May 20, 2021, the entire content of which is incorporated herein by reference.

FIELD

The disclosure relates generally to medical systems and, more particularly, medical systems configured to monitor patient data for risks to patient cardiac health.

BACKGROUND

Some types of medical systems may monitor various data (e.g., a cardiac electrogram (EGM) and activity) of a patient or a group of patients to detect changes in health. In some examples, the medical system may monitor the cardiac EGM to detect one or more types of arrhythmia, such as bradycardia, tachycardia, fibrillation, or asystole (e.g., caused by sinus pause or AV block). In some examples, the medical system may include one or more of an implantable medical device or a wearable device to collect various measurements used to detect changes in patient health.

SUMMARY

Medical systems and techniques as described herein detect risks of cardiovascular events for a patient based upon that patient's data from a glucose sensor. In general, there is a well-defined relationship between a patient's glucose levels and that patient's cardiac health. As demonstrated herein, a variety of medical devices (e.g., implantable devices, wearable devices, etc.) may be configured to monitor patient glucose sensor measurements and one or more computing devices may detect changes in the patient's health that correlate to the glucose sensor measurements. A patient's glucose sensor measurements have been found to provide an accurate assessment of the patient's cardiac health, and monitoring those glucose levels provide an improved indication of changes in the patient's health.

By leveraging a glucose sensor to detect risks to cardiovascular events, the systems, devices, and techniques of the present disclosure may benefit from improved cardiovascular event risk detection, e.g., relative to detection using one or more other patient parameters without considering glucose data. Detection of risk of cardiovascular events using an integrated diagnostics approach may reduce system complexity and provide improved detection relative to separate evaluations of risk based on separate parameters. In view of the above, the present disclosure describes a technological improvement or a technical solution that is integrated into a practical application.

In another implantable monitoring variant, the device is implanted subcutaneously on the cranium to facilitate monitoring additional physiologic signals (e.g., cardiac electrogram (EGM), electroencephalogram (EEG) and activity/ accelerometry) as depicted in FIGS. 1B & 1C. A patient's glucose sensor measurements have been found to provide an accurate assessment of the patient's cardiac health and risk for stroke, hence monitoring those glucose levels provide an improved indication of changes in the patient's health and reduced risk of stroke.

In one example, a medical system comprises processing circuitry communicably coupled to a glucose sensor and configured to generate continuous glucose sensor measurements of a patient. The processing circuitry is further configured to: extract at least one feature from the continuous glucose sensor measurements over at least one time period, wherein the at least one feature comprises one or more of an amount of time within a pre-determined glucose level range, a number of hypoglycemia events, a number of hyperglycemia events, or one or more statistical metrics corresponding to the continuous glucose sensor measurements; apply a machine learning model to the at least one extracted feature to produce data indicative of a risk of a cardiovascular event; and generate output data based on the risk of the cardiovascular event.

In another example, a method comprises, extracting at least one feature from continuous glucose sensor measurements of a patient over at least one time period, wherein the at least one feature comprises one or more of an amount of time within a pre-determined glucose level range, a number of hypoglycemia events, a number of hyperglycemia events, or one or more statistical metrics corresponding to the continuous glucose sensor measurements; applying a machine learning model to the at least one extracted feature to produce data indicative of a risk of a cardiovascular event; and generating an output based on the risk of the cardiovascular event.

In another example, a non-transitory computer-readable storage medium comprises program instructions that, when executed by processing circuitry of a medical system, cause a medical system to: extract at least one feature from continuous glucose sensor measurements of a patient over at least one time period, wherein the at least one feature comprises one or more of an amount of time within a pre-determined glucose level range, a number of hypoglycemia events, a number of hyperglycemia events, or one or more statistical metrics corresponding to the continuous glucose sensor measurements; apply a machine learning model to the at least one extracted feature to produce data indicative of a risk of a cardiovascular event; and generate an output based on the risk of the cardiovascular event.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

Like reference characters denote like elements throughout the description and figures.

DETAILED DESCRIPTION

In general, medical systems according to this disclosure implement techniques for detecting a patient's risk of having cardiovascular events based upon patient data including the patient's glucose levels. Example medical devices that may collect patient data may include an implantable or wearable monitoring device, a pacemaker/defibrillator, or a ventricular assist device (VAD). One example technique includes predicting a risk level of a particular cardiovascular event and whether that risk level further indicates a risk of hospitalization.

The system may include one or more medical devices that may communicate the patient data to other devices, such as a computing device of a cardiac monitoring service, and those devices may further analyze the patient data and then, provide a report regarding the patient's activities and health. The report may compare various implementations of the techniques described herein, for example, comparing, for the same patient, respective glucose sensor measurements values provided by the medical device or another device with a glucose sensor.

In this manner, the techniques of this disclosure may advantageously enable improved accuracy in the detection of changes in patient health and, consequently, better evaluation of the condition of the patient.

Figure 1A:
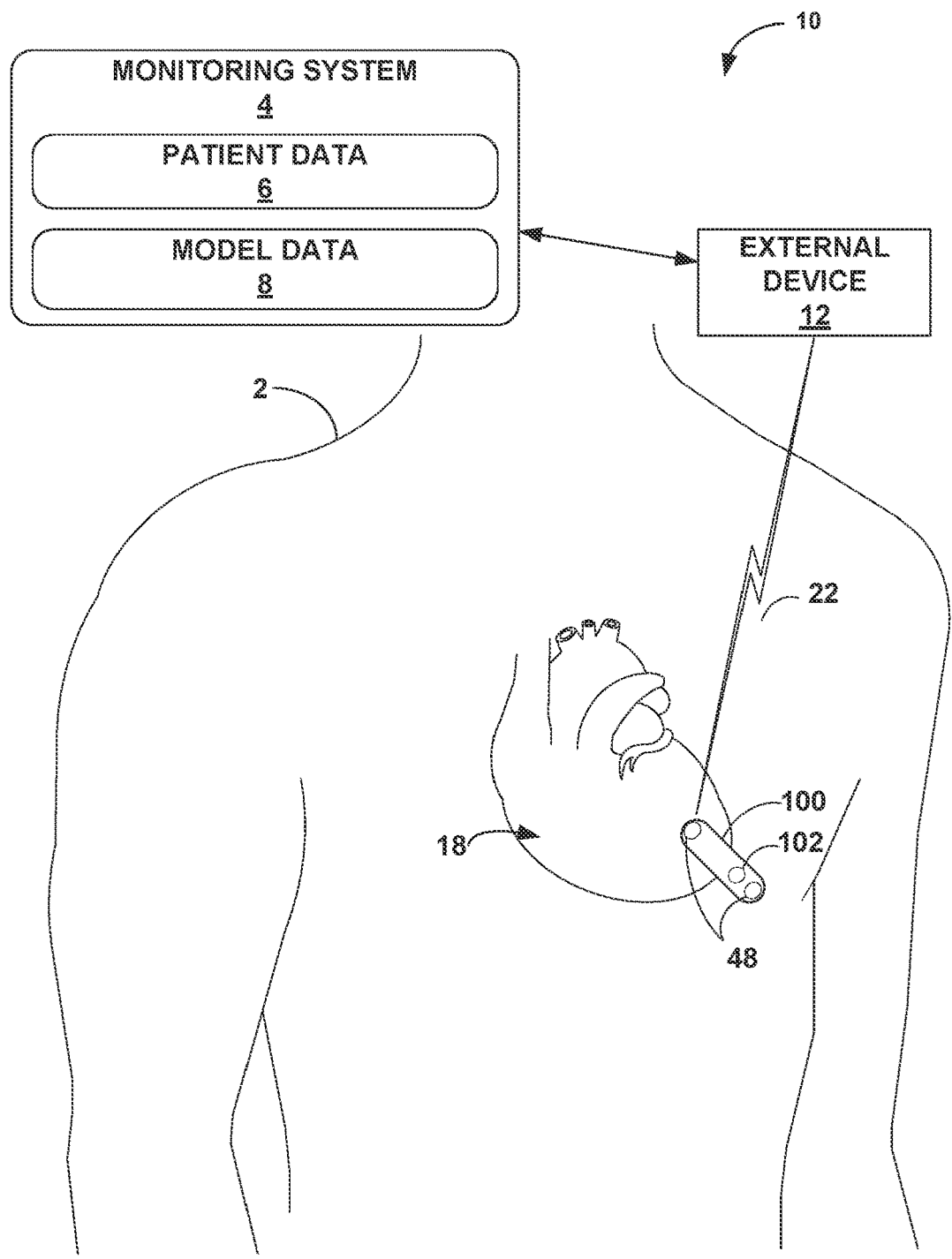
FIG. 1A illustrates example environment of an example medical system in conjunction with a patient, in accordance with one or more examples of the present disclosure.

FIG. 1A is a conceptual drawing illustrating an example medical system 10 in conjunction with a patient 2 according to various examples described in this disclosure. For purposes of this description, knowledge of cardiovascular anatomy and functionality is presumed, and details are omitted except to the extent necessary or desirable to explain the context of the techniques of this disclosure. System 10 includes medical device 100 having optical sensor 102, implanted at or near the site of a heart 18 of a patient 2, and an optional external computing device 12.

Medical device 100 may be in wireless communication with at least one of external device 12 and other devices not pictured in FIG. 1. In some examples, medical device 100 is implanted outside of a thoracic cavity of patient 2 (e.g., subcutaneously in the pectoral location illustrated in FIG. 1A). In other examples, medical device 100 is implanted subcutaneously outside of the cranium of patient 2 (e.g., subcutaneously in the cranial location illustrated in FIG. 1C and FIG. 1D for medical devices 100A and 100B, respectively. Medical device 100 may be positioned near the sternum near or just below the level of the heart of patient 2, e.g., at least partially within the cardiac silhouette. In some examples, medical device 100 includes a plurality of electrodes 48, and is configured to sense electrical activity of patient 2's heart via plurality of electrodes 48. The sensed electrical activity may be herein referred to as an electrocardiogram (ECG) or a cardiac electrogram (EGM). In some examples, medical device 100 takes the form of the LINQ™ ICM, CraniaLINQ™ INM, or another ICM similar to, e.g., a version or modification of, the LINQ™ ICM. Therefore, in some embodiments, medical device 100 may serve as a combination sensor device suitable for monitoring and/or facilitating treatment of multiple conditions. For example, in embodiments such as the LINQ™ embodiments described herein, the medical device 100 may serve as a combination of a glucose sensor and/an cardiac EGM or cardiac monitoring device that may be uniquely suited for monitoring patient comorbidities. Although described primarily in the context of examples in which medical device 100 is an ICM, in various examples, medical device 100 may represent a cardiac monitor, a neuro monitor, a defibrillator, a cardiac resynchronization pacer/defibrillator, a pacemaker, an implantable pressure sensor, a neurostimulator, or any other implantable or external medical device that may, for example, have appropriate access to an analyte. Furthermore, although described in the context of examples in which a single medical device includes functionality for sensing other patient parameters, e.g., cardiac EGM or patient activity parameters, in addition to glucose levels, in some examples the techniques of this disclosure may be implemented in systems including a plurality of medical devices, which may be implantable or external, and which may respectively sense one or more patient parameters.

External device 12 may be a computing device with a user interface, such as a display viewable by the user and an interface for providing input to external device 12 (i.e., a user input mechanism). In some examples, external device 12 may be a notebook computer, tablet computer, workstation, one or more servers, smartphone, smartwatch, smart injection pen (such as, for example the InPen™ device available from Companion Medical, Inc. and Medtronic MiniMed, Inc.), insulin pump (such as for example, any one of the MiniMed™ 630G System, MiniMed™ 670G System, or MiniMed™ 770G System available from Medtronic MiniMed, Inc.), personal digital assistant, or another computing device that may run an application that enables the computing device to interact with medical device 100. External device 12 is configured to communicate with medical device 100 and, optionally, another computing device (not illustrated in FIG. 1), via wireless communication. External device 12, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets (including but not limited to BLE), or other communication technologies operable at ranges greater than near-field communication technologies).

External device 12 may be used to configure operational parameters for medical device 100. External device 12 may be used to retrieve data from medical device 100. The retrieved data may include values of physiological parameters measured by medical device 100, indications of episodes of arrhythmia or other maladies detected by medical device 100, and physiological signals recorded by medical device 100. For example, external device 12 may retrieve analyte concentrations recorded by medical device 100, e.g., due to medical device 100 determining that a change in analyte concentration exceeded a predetermined magnitude, or that predetermined maximum or minimum analyte concentration threshold was exceeded, during the segment, or in response to a request to record the segment from patient 2 or another user. Additionally, or alternatively, external device 12 may retrieve analyte concentrations, cardiac EGM segments recorded by medical device 100, e.g., due to medical device 100 determining that an episode of arrhythmia or another malady occurred during the segment, or in response to a request to record the segment from patient 2 or another user. In some examples, one or more remote computing devices may interact with medical device 100 in a manner similar to external device 12, e.g., to program medical device 100 and/or retrieve data from medical device 100, via a network such as a cloud computing network suitable for storing and processing data for the benefit of patients and/or health care providers, such as, for example, the CareLink™ Diabetes therapy management system available from Medtronic MiniMed, Inc.

In various examples, medical device 100 may include one or more additional sensor circuits configured to sense a particular physiological or neurological parameter associated with patient 2, or may include a plurality of sensor circuits, which may be located at various and/or different positions relative to patient 2 and/or relative to each other, and may be configured to sense one or more physiological parameters associated with patient 2.

For example, medical device 100 may include a sensor operable to sense a body temperature of patient 2 in a location of the medical device 100, or at the location of the patient where a temperature sensor coupled by a lead to medical device 100 is located. In another example, medical device 100 may include a sensor configured to sense motion, such as steps taken by patient 2 and/or a position or a change of posture of patient 2. In various examples, medical device 100 may include a sensor that is configured to detect breaths taken by patient 2. In various examples, medical device 100 may include a sensor configured to detect heartbeats of patient 2. In various examples, medical device 100 may include a sensor that is configured to measure systemic blood pressure of patient 2.

In some examples, one or more of the sensors of medical device 100 may be implanted within patient 2, that is, implanted below at least the skin level of the patient. In some examples, one or more of the sensors of medical device 100 may be located externally to patient 2, for example as part of a cuff or as a wearable device, such as a device imbedded in clothing that is worn by patient 2. In various examples, medical device 100 may be configured to sense one or more physiological parameters associated with patient 2, and to transmit data corresponding to the sensed physiological parameter or parameters to external device 12, as represented by the lightning bolt 22 coupling medical device 100 to external device 12.

Transmission of data from medical device 100 to external device 12 in various examples may be performed via wireless transmission, using for example any of the formats for wireless communication described above. In various examples, medical device 100 may communicate wirelessly to an external device (e.g., an instrument or instruments) other than or in addition to external device 12, such as a transceiver or an access point that provides a wireless communication link between medical device 100 and a network. Examples of communication techniques used by any of the devices described herein may include radiofrequency (RF) telemetry, which may be an RF link established via Bluetooth®, BLE, Wi-Fi, or medical implant communication service (MICS).

In some examples, system 10 may include more or fewer components than depicted in FIG. 1. For example, in some examples, system 10 may include multiple additional implantable medical devices (IMDs), such as implantable pacemaker devices or other IMDs, implanted within patient 2. In these examples, medical device 100 may function as a hub device for the other IMDs. For example, the additional IMDs may be configured to communicate with the medical device 100, which would then communicate to the external device 12, such as a user's smartphone, via a low-energy telemetry protocol.

In system 10, monitoring system 4 is an example of a medical system configured to enhance functionality of medical device 100 with machine learning computing services. In some examples, monitoring system 4 leverages (continuous) glucose sensing capabilities of medical device 100 to generate glucose sensor measurements of patient 2 and then, using a machine learning model, determine whether those measurements (and in some examples other patient parameter values) indicate patient 2's risk (e.g., risk level) of a cardiovascular event. Monitoring system 4 may combine, into patient data 6, these (e.g., continuous) glucose sensor measurements with other data. As an alternative, monitoring system 4 may receive glucose sensor measurements from another glucose sensor, such as a glucose sensor in a wearable cardiac monitor or a continuous glucose sensor (e.g., a continuous glucose monitoring (CGM) sensor) independent of the glucose sensor in medical device 100.

In some examples, patient data 6 may include datasets of input features for use by the machine learning model defined in model data 8. Monitoring system 4 may store a representation of the model (e.g., a neural network) such that logic may identify model components, including a prediction algorithm, input features to feed into the prediction algorithm, and output classes generated by the prediction algorithm. There are number of applicable machine learning concepts that monitoring service 4 may consider in designing a prediction algorithm; in general, the prediction algorithm executes a technique to map the input features (X) to labels of a label distribution defined by one or more mathematical functions (e.g., linear or non-linear equations) and/or one or more statistics (e.g., prior or conditional probabilities).

Monitoring system 4 may utilize processing circuitry to execute the above logic and instantiate the machine learning computing service. In some examples, monitoring service 4 may run the machine learning computing service on a computing device in communication with medical device 100, such as external device 12 or another external device, such as local computer coupled to medical device 100 by a wired/wireless connection or a remote server coupled to medical device 100 by a network connection. It should be noted that the present disclosure may describe a glucose monitor as including a glucose sensor, a cardiac monitor, or a computing device in communication with at least one of the glucose monitor or the cardiac monitor and that glucose monitor may be in reference to medical device 100, external device 12, the other external device mentioned above, or any other computing device that comprises the above processing circuitry. FIGS. 1A, 1C, and 1D, in particular, illustrates medical device 100 as an example cardiac monitor that includes the glucose sensor (e.g., a functional component). It should be noted that there are number of other ways to combine glucose sensing and cardiac monitoring.

In response to patient data 6 including patient 2's glucose sensor measurements, the above processing circuitry is configured to extract at least one feature corresponding to at least one time period. A number of possible features are envisioned by the present disclosure of which some examples include one or more of an amount of time within a pre-determined glucose level range (e.g., range time), a number of hypoglycemia events (e.g., hypoglycemic event count), or a number of hyperglycemia events (e.g., hyperglycemic event count). The amount of time within a pre-determined glucose level range includes an amount of time in a first (e.g., healthy) glucose range or a second (e.g., unhealthy) glucose range.

Other possible features include one or more of a variety of statistical metrics corresponding to the continuous glucose sensor measurements, such as a standard deviation, a coefficient of variation, an average, a median, an interquartile range, a maximum rate of change of at least one dataset of the continuous glucose sensor measurements, and/or the like. The at least one dataset includes different time intervals of the continuous glucose sensor measurements. It should be noted that there are a number of other possible features that can be input for the machine learning model. To illustrated by way of example, the above processing circuitry may be configured to extract at least one glucose sensor measurement feature and at least one cardiac feature to produce the data indicative of the risk of a cardiovascular event. Examples of cardiac features correspond to impedance and/or electrocardiogram (EGM) metrics, including impedance, respiratory rate, night heart rate, heart rate variability, activity, or atrial fibrillation (AF) parameters.

In some examples, model data 8 defines the machine learning model as mathematical function(s) for a univariate regression analysis or probability distribution(s) for a Bayesian Belief Net. In most (if not all) examples, model data 8 further defines the machine learning model using different feature combinations (e.g., with a maximum of 6-8 features) and different output classes (e.g., low, medium, high evidence states/risk levels for the cardiovascular event). In one example, model data 8 defines the model using the following features: An amount of time in first glucose range (e.g., 90-140 which may be referred to as "normal" or healthy) in last 7 days and in last 30 days and in last 90 days; number of hypoglycemia events in last 7 days and in last 30 days and in last 90 days; time in low range (<90) in last 7 days and in last 30 days and in last 90 days; an amount of time in second glucose range (greater than or equal to 140 which may be referred to as unhealthy) in last 7 days and in last 30 days and in last 90 days; standard deviation of glucose sensor measurements in last 7 days and in last 30 days and in last 90 days; coefficient of variation of glucose sensor measurements in last 7 days and in last 30 days and in last 90 days; average glucose sensor measurements in last 7 days and in last 30 days and in last 90 days; median glucose sensor measurements in last 7 days and in last 30 days and in last 90 days; interquartile range of glucose sensor measurements in last 7 days and in last 30 days and in last 90 days; and average and/or maximum rate of change in glucose sensor measurements in last 7 days and in last 30 days and in last 90 days.

By training the machine learning model, criterion (e.g., thresholds) may be determined for evaluating the above features. According to one example implementation of a trained machine learning model, model data 8 may combine at least two of the above features such that if the range time feature for an amount of time in the first glucose range (e.g., normal range (90-140)) in last 30 days is less than 40% or a number of hypoglycemia events feature in last 7 days is less than 1 or the range time feature of an amount of time in the second glucose range (e.g., high or unhealthy range) in last 30 days is greater than 80%, the model predicts a high risk level of a cardiovascular event. Furthermore, if the above criteria are not satisfied (e.g., not high risk), model data 8 further defines the following criteria: If a standard deviation of measurements in last 30 days greater than a threshold or the number of hypoglycemia events features in last 30 days greater than one or the range time feature of an amount of time in the second glucose range (e.g., high or unhealthy range) in last 30 days is greater than 30% or the range time feature for an amount of time in the first glucose range (e.g., normal range (90-140)) in last 30 days is less than 60%, there is a medium risk of a cardiovascular event for patient 2. If none of the above criteria are satisfied, the model predicts that a low risk level for patient 2.

In some examples, model data 8 may specify a subset of the above features for predicting a risk of a cardiovascular event. Based on various metrics, features may be compared to each other with respect to their relevance to patient 2's cardiovascular health. In response to the comparison, one or more features may be removed from the machine learning model, for example, if a feature fails to provide enough orthogonal information. For example, the machine learning model may be configured with features restricted to the following 6 parameters: Time in normal range (90-140) in last 30 days, Number of hypoglycemia events in last 30 days, Number of hypoglycemia events in last 7 days, Time in high range in last 30 days, Standard deviation of BG measurements in in last 30 days, Maximum rate of change in BG measurements in last 7 days. Different combinations of these features may define low, medium, and high evidence states for patient 2's blood glucose levels.

The above processing circuitry is configured to apply the machine learning model to the at least one extracted feature to produce data indicative of a risk of a cardiovascular event and generate an output based on the risk of the cardiovascular event. If a classifier-based model is applied, model data 8 stores, for each input feature, one or more prior probabilities and one or more posterior probabilities. A prior probability may be based on knowledge, such as a large data corpus, and then, approximated or assumed. A posterior probability may be based on one or more conditions or observations of the input feature itself. The above processing circuitry of monitoring service computes a likelihood measuring the goodness of fit of the classifier-based model to values of the at least one extracted feature. In some examples, the above processing circuitry generates a joint probability distribution of multiple features with unknown values and sets forth one or more criterion for predicting the risk of a cardiovascular event. Given a set of known input feature values for patient 2, the above processing circuitry computes a joint probability as the likelihood of patient 2's risk of a cardiovascular event and then, determines whether that joint probability satisfies based on the above criterion. Based on that determination, the above processing circuitry generates output data corresponding to patient 2's risk of a cardiovascular event— such as a risk level and/or whether that risk level is further indicative of some aspect (e.g., a risk of hospitalization) due to the cardiovascular event—and communicates that output data to a computing device over a wired or wireless connection.

The present disclosure may refer to specific examples, but those examples do not limit the machine learning model or the machine learning computing service described herein. The present disclosure also does not limit the cardiovascular event to any specific example(s) and may include any condition affecting a human heart or blood vessels that pump and move blood around a human body (e.g., patient 2's circulatory system); hence, cardiovascular event, as defined herein, may be a general term to represent such conditions. To determine patient 2's risk of the cardiovascular event without of relying (e.g., exclusively) on cardiac physiological signals (e.g., cardiac electrogram (EGM), electroencephalogram (EEG) and activity/accelerometry), the techniques described in the present disclosure leverage patient 2's glucose sensor measurements.

As mentioned above, the machine learning model is configured to determine (e.g., predict) patient 2's risk level of a cardiovascular event. In some examples, the above processing circuitry generates output data indicative of patient 2's risk of hospitalization due to some cardiovascular event (e.g., including any cardiac-neurogenic event, such as an ischemic or a hemorrhagic stroke). When implemented in external device 12, the above processing circuitry may communicate, to medical device 100 or another medical device (e.g., a cardiac monitor or a glucose monitor), the output data indicative of the above hospitalization risk over a network connection or a direct connection. The above processing circuitry may also communicate the output data to a cardiac monitoring service, such as monitoring service 4, over a wireless network connection. In some examples, external device 12 generates and communicates, to medical device 100 or the other medical device, output data indicative of patient 2's risk of at least one of cardiac inflammation, heart failure, an arrhythmia, or a stroke. In other examples, external device 12 computes a likelihood probability (e.g., a joint probability) that a glucose level (e.g., a recent/current measurement or a historical reading) of patient 2 causes any of the above-mentioned cardiovascular events.

In some examples where medical device 100 (or another device with a cardiac monitor) receives the above output data, that device generates second output data indicative of the risk of the cardiovascular event based on the received output data and further based on data corresponding to at least one of impedance or cardiac EGM metrics. As described herein, these metrics specify criteria (e.g., thresholds) for impedance, respiratory rate, night heart rate, heart rate variability, cardiac activity, or atrial fibrillation (AF) parameters, and satisfaction of the specified criterion indicates a particular risk level of the cardiovascular event.

In some examples, external device 12, medical device 100 (or the above cardiac monitor) apply a second machine learning model to at least one second feature to produce second data indicative of the risk of a cardiovascular event. Examples of the second feature may include any of the above examples of cardiac features. Similar to the machine learning model employed by monitoring service 4, the second machine learning model computes a likelihood probability that a glucose level (e.g., a recent/current measurement or a historical reading) of patient 2 is a cause behind the risk of the cardiovascular event.

As described herein, monitoring service 4 configures a computing device, such as external device 12, to run a machine learning computing service to provide patient 2 with remote cardiac monitoring and in some examples, customize the computing service for patient 2 (e.g., patient 2's cardiac physiology or physiology in general). In addition to applying a machine learning model to patient 2's feature data, monitoring service 4 configures the customized computing service to update the machine learning model, personalizing the model's prediction algorithm to patient's cardiac activity and/or glucose metabolism. In one example, when processing circuitry of the above computing device applies (e.g., a current version of) the machine learning model, the processing circuitry computes a likelihood probability that a glucose level of the patient causes the cardiovascular event and then, incorporate the likelihood probability into the machine learning model, updating the current version of that model. The processing circuitry may incorporate the likelihood probability into the model in a number of ways, such as by at least one including the likelihood probability in the at least one feature, including the likelihood probability as an independent prior probability, or adjusting at least one prior probability for the cardiovascular event.

Figure 1B:
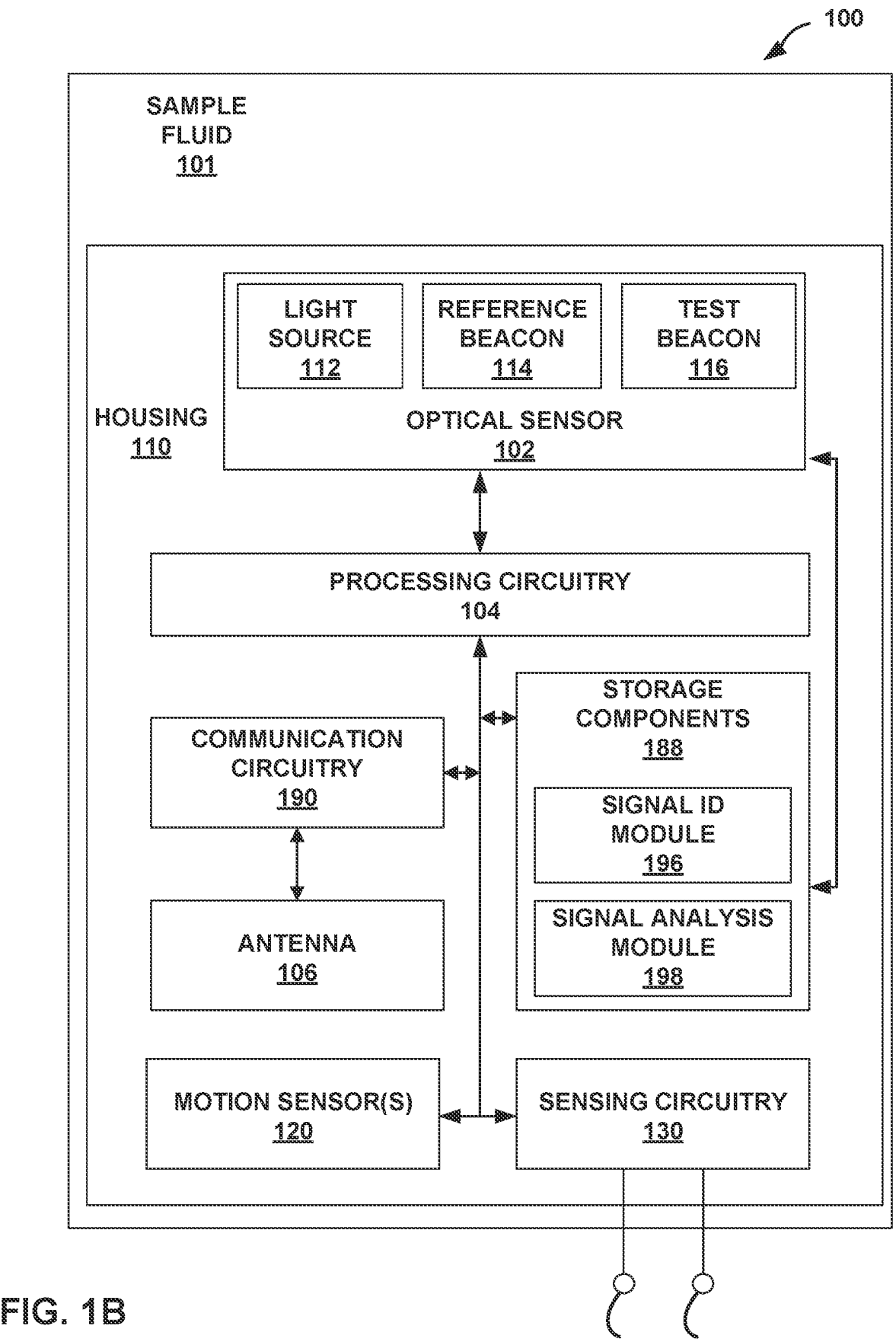
FIG. 1B illustrates an example medical device for use by the example medical system of FIG. 1A, in accordance with one or more examples of the present disclosure.
Figure 1C:
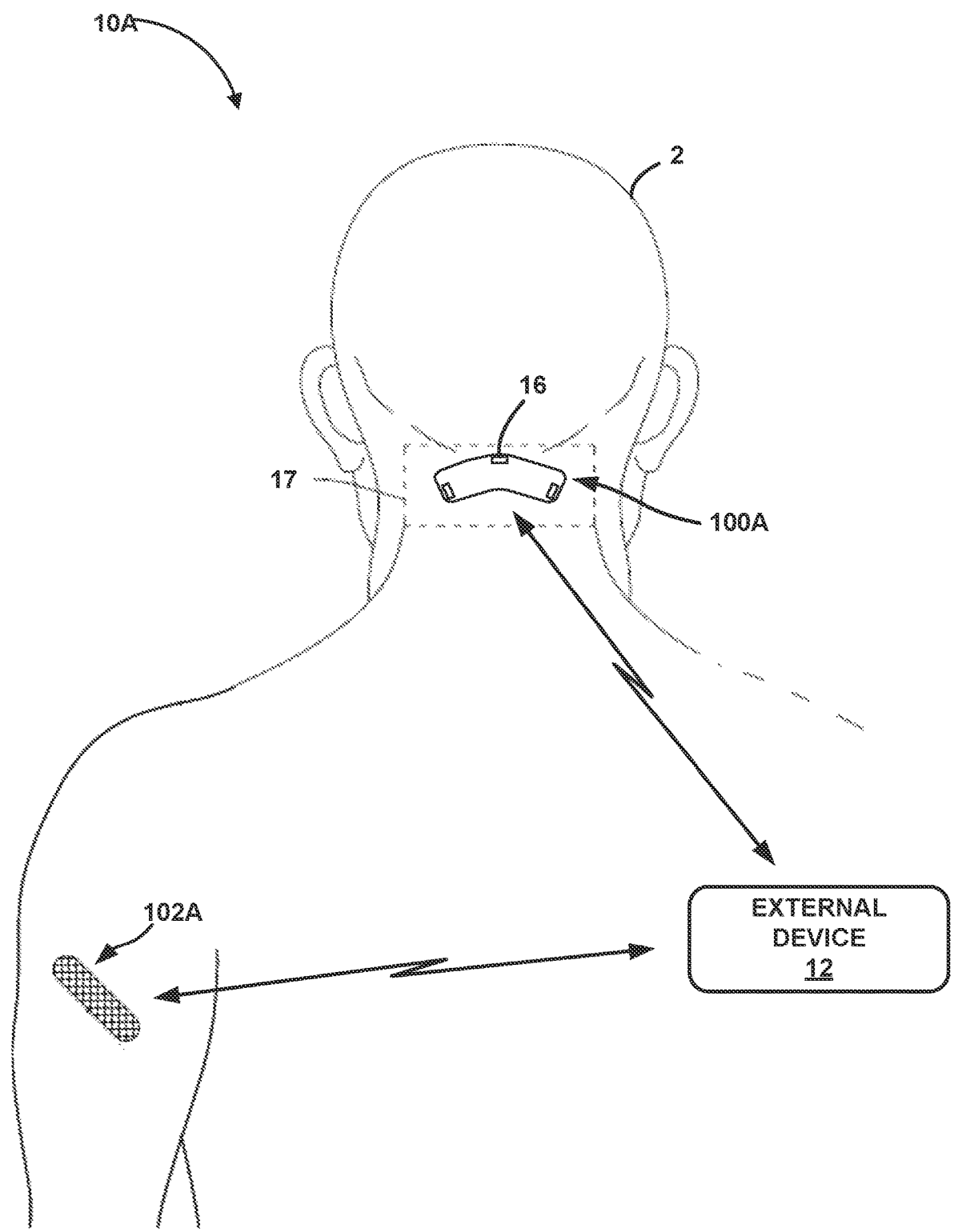
FIG. 1C illustrates another example environment of an example medical system in conjunction with a patient, in accordance with one or more examples of the present disclosure.
Figure 1D:
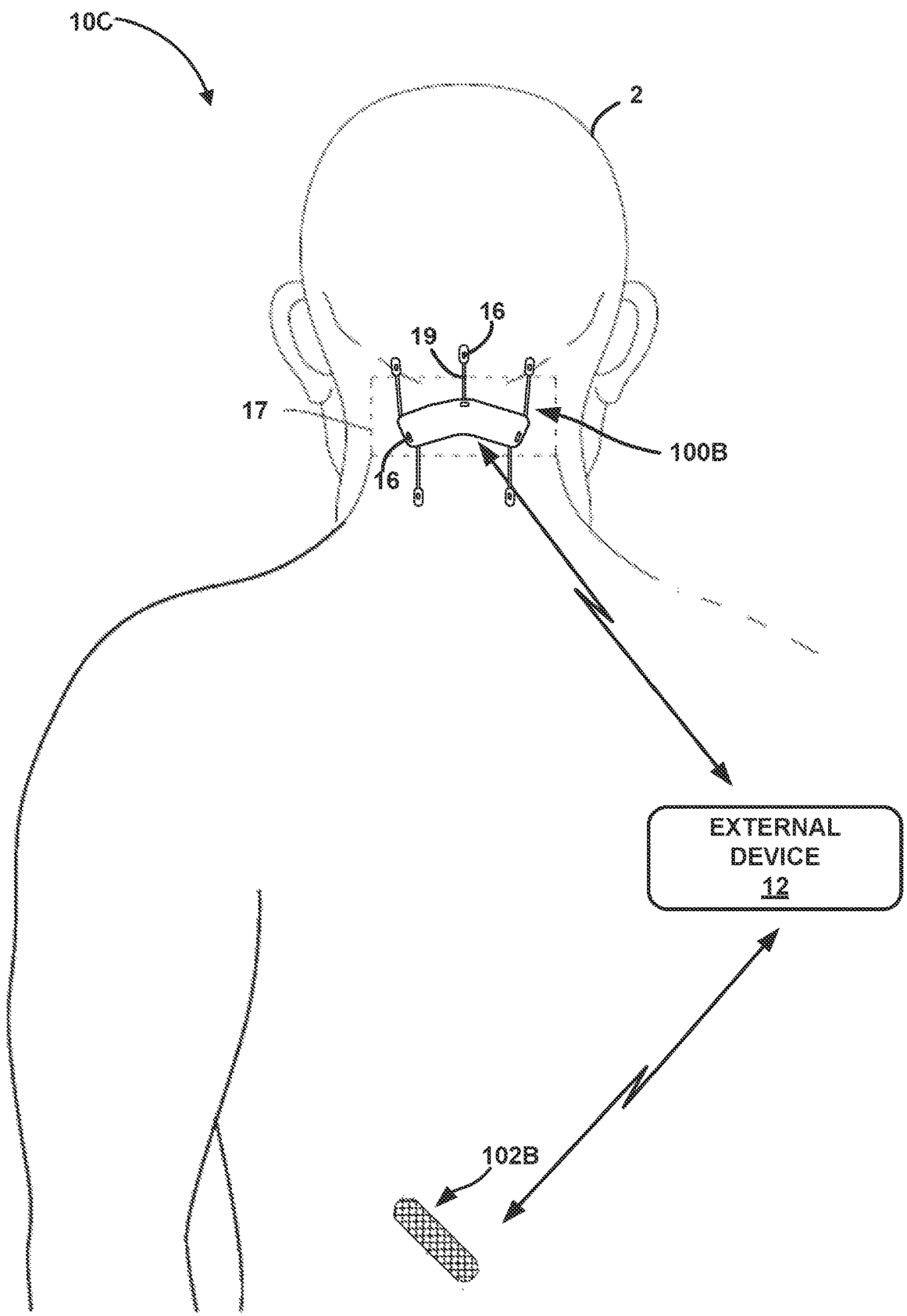
FIG. 1D illustrates yet another example environment of an example medical system with electrode extensions in conjunction with a patient, in accordance with one or more examples of the present disclosure.

FIG. 1B is a conceptual diagram illustrating a schematic and conceptual diagram of medical device 100 including optical sensor 102. In addition to the above described functionality, medical device 100 is configured to optically measure a concentration of one or more analytes in a sample fluid 101 of a biological system, such as a concentration of glucose of a human patient. Although described for detecting a concentration of glucose, in other examples, medical device 100 may be configured to measure a concentration of other analytes such as, for example, one or more of sodium, chloride, potassium, bicarbonate/carbon dioxide, blood urea nitrogen, creatinine, glucose, brain natriuretic peptide, C-reactive protein, troponin I, lactate, pH, or L-dopa. Sample fluid 101 may include, but is not limited to, one or more of blood, interstitial fluid, saliva, urine, spinal fluid, peritoneal fluid, or other bodily fluids.

Medical device 100 includes optical sensor assembly 102 (e.g., optical sensor 102), processing circuitry 104, an antenna 106, and housing 110. Medical device 100 may be insertable into a biological system. For example, medical device 100 may be transcutaneously insertable or implantable in interstitial fluid or a body cavity of a human patient or subcutaneously insertable or implantable under a scalp or on a cranium of the human patient. In other examples, a first portion of medical device 100 may be inserted into the skin, e.g., exposed to or otherwise in fluidly coupled to an interstitial fluid of the patient, and a second portion of the medical device may be affixed to or worn by the patient, e.g., as a skin worn patch. In this way, medical device 100 may enable continuous or near continuous monitoring of one or more analyte concentrations in the biological system.

Optical sensor 102 includes light source 112, reference optical beacon 114, and test optical beacon 116. Optical sensor 102 is configured to detect a fluorescence emitted by a fluorophore in response to exposure to an analyte, and produce a signal indicative of the concentration of the analyte. Optical signals acquired subcutaneously under the scalp or on the cranium provide a stable transmission of analyte concentration information for a period of time.

Light source 112 includes one or more radiation sources configured to emit radiation having a selected wavelength range. For example, light source 112 may include one or more light emitting diodes (LEDs) or LASERs. In some examples, light source 112 may include two, three, four, five, or more LEDs arrange on an LED chip. Radiation emitted by light source 112 may include any suitable wavelength or range of wavelengths of radiation. In some examples, the radiation may include wavelengths in the visible range, e.g., within a range from about 380 nanometers (nm) to about 740 nm.

In some examples, light source 112 may emit radiation having a range of wavelengths selected based on an absorbance of a fluorophore of reference optical beacon 114 and/or test optical beacon 116. For example, the absorbance of the fluorophore may be substantially within a range from about 480 nm to about 700 nm. As used herein, absorbance substantially within a particular wavelength range may include a percentage of absorption within the range relative to a total absorption spectrum that is greater than 90%, such as greater than 95% or greater than about 99%. In such examples, light source 112 may have an emission spectrum substantially within a range from about 480 nm to about 700 nm. As used herein, an emission spectrum substantially within a particular wavelength range may include a percentage of emission within the range relative to a total emission spectrum that is greater than 90%, such as greater than 95% or greater than about 99%. As another example, the fluorophore may have a maximum absorbance peak of less than about 600 nm, such as about 590 nm. In such examples, light source 112 may have a peak emission wavelength of about 590 nm.

In examples in which light source 112 includes one or more LEDs with an emission wavelength greater than about 580 nm, light source 112 may include one or more LEDs driven by less than about 100 milliamps and/or a voltage within a range from about 1.5 volts (V) to about 2.5 V, such as from about 1.9 V to about 2.2 V. By driving light source 112 in the milliamp range, with less than about 2.5 V, and/or with an emission wavelength greater than about 580 nm, light source 112 may include a less complex circuit compared to an LED configured to emit light having a wavelength less than about 580 nm.

The radiation may be incident on a respective fluorophore of reference optical beacon 114 and test optical beacon 116. In response to the incident radiation, the respective fluorophore of reference optical beacon 114 and test optical beacon 116 may fluoresce. The respective fluorophores may include any suitable fluorophore. Example fluorophores include, but are not limited to, ruthenium-tris(4,7-diphenyl-1,10-phenanthroline) dichloride (Ru(dpp)), platinum(II) octaethylporphyrin (PtOEP), palladium(II) octaethylporphyrin (PdOEP), platinum(II)-5,10,15,20-tetrakis-(2,3,4,5,6-pentafluorphenyl)-porphyrin (PtTFPP), palladium(II)-5,10,15,20-tetrakis-(2,3,4,5,6-pentafluorphenyl)-porphyrin (PdTFPP), platinum(II) octaethylporphyrinketone (PtOEPK), palladium(II) octaethylporphyrinketone (PdOEPK), platinum(II) tetraphenyltetrabenzoporphyrin (PtTPTBP), palladium(II) tetraphenyltetrabenzoporphyrin (PtTPTBP), platinum(II) tetraphenyltetranaphthoporphyrin (PtTPTNP), or palladium(II) tetraphenyltetranaphthoporphyrin (PdPTPNP).

In some examples, a fluorophore may be selected to have a relatively higher light-emission efficiency, relatively higher brightness, and relatively longer emission time constant, compared to other fluorophores configured to interact with oxygen. In some examples, a fluorophore may be selected to fluoresce at a wavelength of about 580 nm or longer. In some examples, a fluorophore may be selected to have an emission wavelength within a range from about 600 nm to about 1100 nm and/or to match a peak sensitivity range for a silicon photodetector. In some examples, a fluorophore may be selected to be biocompatible and/or intrinsically stable for chronic use in vivo. The respective fluorophore of reference optical beacon 114 and test optical beacon 116 may have the same chemical composition or a different chemical composition.

The fluorophore may be configured to interact with a substance present in sample fluid 101 surrounding medical device 100. In some examples, the respective fluorophore of reference optical beacon 114 and test optical beacon 116 may be positioned on an external surface of housing 110 of medical device 100. In other examples, housing 110 may include one or more apertures fluidly coupling at least the respective fluorophore of reference optical beacon 114 and test optical beacon 116 to sample fluid 101. In these ways, the respective fluorophore of reference optical beacon 114 and test optical beacon 116 may be in contact with sample fluid 101.

In some examples, the fluorophore may interact with oxygen present in sample fluid 101. For example, a fluorescence of the respective fluorophores may be quenched by oxygen. In other words, a higher concentration of oxygen proximate test optical beacon 116 may cause the fluorophore of test optical beacon 116 to emit a lesser intensity of fluorescence compared to the fluorescence of the fluorophore of a reference optical beacon 114 that is proximate to a relatively lower concentration of oxygen. In this way, the fluorescence of the fluorophore of reference optical beacon 114 and test optical beacon 116 may be used to determine a variation in a concentration of the substance proximate each respective fluorophore.

For example, reference optical beacon 114 may be used to adjust for an ambient concentration of a substance, such as oxygen, in sample fluid 101, whereas test optical beacon 116 may include an additional chemistry configured to react with a selected analyte to change a concentration of the substance proximate to test optical beacon 116. In some examples, in addition to the fluorophore, test optical beacon 116 includes a reagent substrate configured to react with a selected analyte to change a concentration of the substance proximate to test optical beacon 116. The reagent substrate may include one or more enzymes, catalysts, antibodies, molecular imprinted polymers, aptamers, or other materials configured to react with an analyte to modulate a concentration of a selected substance.

In examples in which the analyte includes glucose, the reagent substrate may include glucose oxidase and catalase. For example, the glucose oxidase consumes oxygen (e.g., the substance) to oxidize glucose present in sample fluid 101 to yield gluconic acid and hydrogen peroxide (e.g., a bi-product). The catalase reduces the hydrogen peroxide to yield water and oxygen (e.g., the substance). By consuming the hydrogen peroxide, catalase may reduce or prevent inhibition of glucose oxidase by the hydrogen peroxide. By consuming oxygen via glucose oxidase and producing oxygen via catalase, the reagent substrate is configured to modulate a local oxygen concentration that is indicative of the concentration of glucose.

In some examples, reference optical beacon 114 and/or test optical beacon 116 may include limiting membrane and/or a selective ion transfer membrane disposed on the fluorophore and/or the reagent substrate. The membrane may be selectively permeable to the analyte. For example, the membrane may control a rate of diffusion of the analyte from sample fluid 101 to a reagent substrate of test optical beacon 116. In this way, the membrane may control an extent of reaction or a rate of reaction of the analyte at a surface of the reagent substrate, e.g., by controlling a rate of exposure of the reagent substrate to the analyte. Additionally, or alternatively, the membrane may extend a linear range of a respective optical beacon, e.g., relative to a glucose concentration in the sample fluid 101, by limiting a permeability of glucose. In other words, the membrane may prevent saturation of the reagent substrate (e.g., enzymes of the reagent substrate) over a greater range of glucose concentrations relative to an optical beacon without a reagent substrate. In this way, the chemistry of the fluorophore, reagent substrate, and/or membrane may be selected to be specific to the analyte, extend a linear range of the respective optical beacon, and/or increase a useable life of the respective optical beacon.

Reference optical beacon 114 and test optical beacon 116 each include a respective photoreceptor in line-of-sight with the respective fluorophore. The respective photodetector of reference optical beacon 114 and test optical beacon 116 are configured to detect a respective intensity of the respective fluorescence of the fluorophore for each of reference optical beacon 114 and test optical beacon 116. Although described as including two photodetectors, in some examples, optical sensor 102 may include a single photodetector, each of reference optical beacon 114 and test optical beacon 116 being disposed on a portion of the single photodetector. The respective photodetectors may include any suitable photodetector. In some examples, the photodetectors may include flip-chip photodetectors. The respective photodetectors may be selected to detect a wavelength or a range of wavelengths of radiation emitted by the respective fluorophore of reference optical beacon 114 and test optical beacon 116. For example, in response to radiation emitted from light source 112 incident on the fluorophore, the fluorophore may have an emission spectrum substantially within a range from about 700 nm to about 820 nm, and/or a maximum emission peak of about 760 nm. In such examples, the photodetector may be configured to detect radiation within a range from about 380 nm to about 1100 nm, such as within a range from about 700 nm to about 820 nm, and/or with a peak detection sensitivity of within a range from about 700 nm to about 820 nm. In some examples, the peak detection sensitivity may be an intrinsic property of the photodetector, e.g., based on materials of construction and/or physical configuration. In some examples, the detection range or peak detection sensitivity of the photodetector may be modulated by, for example, one or more filters, such as a bandpass filter, a light absorbing gel or film, or other discrete filter between a fluorophore and a respective photodetector. Filtering may, for example, enable a photodetector to detect a fluorescence of a fluorophore, while substantially not detecting light emitted by a light source.

The respective photodetectors may transmit a signal indicative of the respective intensity to processing circuitry 104. Processing circuitry 104 may include various types of hardware, including, but not limited to, microprocessors, controllers, digital signal processors (DSPs), application specific integrated circuits (ASICs), field-programmable gate arrays (FPGAs), or equivalent discrete or integrated logic circuitry, as well as combinations of such components. The term "processing circuitry" may generally refer to any of the foregoing logic circuitry, alone or in combination with other logic circuitry, or any other equivalent circuitry. In some examples, processing circuitry 104 may represent and/or include additional components. Processing circuitry 104 represents hardware that can be configured to implement firmware and/or software that sets forth one or more of the algorithms described herein. For example, processing circuitry 104 may be configured to implement functionality, process instructions, or both for execution of processing instructions stored within one or more storage components 188, such as signal identification module 196 and/or signal analysis module 198.

One or more storage components 188 may be configured to store information within medical device 100. One or more storage components 188, in some examples, include a computer-readable storage medium or computer-readable storage device. In some examples, one or more storage components 188 include a temporary memory, meaning that a primary purpose of one or more storage components 188 is not long-term storage. One or more storage components 188, in some examples, include a volatile memory, meaning that one or more storage components 188 does not maintain stored contents when power is not provided to one or more storage components 188. Examples of volatile memories include random access memories (RAM), dynamic random-access memories (DRAM), ferroelectric random-access memories (FRAM), static random-access memories (SRAM), and other forms of volatile memories known in the art. In some examples, one or more storage components 188 are used to store program instructions for execution by processing circuitry 104. One or more storage components 188, in some examples, are used by software or applications running on processing circuitry 104 to temporarily store information during program execution.

In some examples, one or more storage components 188 may be configured for longer-term storage of information. In some examples, one or more storage components 188 may include non-volatile storage elements. Examples of such non-volatile storage elements include flash memories, or forms of electrically programmable memories (EPROM) or electrically erasable and programmable memories (EEPROM).

Processing circuitry 104, e.g., signal identification module 196, may be configured to identify a respective signal corresponding to a respective optical beacon. For example, signal identification module 196 may include a multiplexer configured to select between inputs from reference optical beacon 114 and test optical beacon 116. In some examples, input selection maybe based on a timing of light emitted by light source 112. For example, in response to a first light pulse emitted from light source 112, processing circuitry 104, e.g., signal identification module 196, may select an input from reference optical beacon 114 that is then output to processing circuitry 104 and/or signal analysis module 198 for processing. In response to a second light pulse emitted from light source 112 that is separated in time from the first light pulse, processing circuitry 104, e.g., signal identification module 196, may select an input from test optical beacon 116 that is then output to processing circuitry 104 and/or signal analysis module 198 for processing. In some examples, a duration between the first light pulse and the second light pulse may be greater than 1 millisecond, greater than 10 milliseconds, greater than 100 milliseconds, greater than one second, or more. For example, the duration between the first light pulse and the second light pulse may be based on a duration of fluorescence of the respective fluorophore in response to the first light pulse.

Processing circuitry 104, e.g., via signal analysis module 198, may be configured to process the identified signal to determine a concentration of an analyte. In some examples, signal analysis module 198 may be coupled to one or more capacitors configured to receive from a respective photodetector of reference optical beacon 114 or test optical beacon 116 a respective amount of electrical energy indicative of a fluorescence emission from a respective fluorophore. Processing circuitry 104, e.g., signal analysis module 198, may determine a difference between a first amount of electrical energy associated with a fluorescent decay of the fluorophore of reference optical beacon 114 and a second amount of electrical energy associated with a fluorescent decay of the fluorophore of test optical beacon 116. The fluorescent decay of the respective fluorophores may include substantially all fluorescence emitted by the respective fluorophore in response to incident light emitted by light source 112, such as at least 80%, at least 90%, at least 95%, or at least 99% of a total fluorescent decay of the respective fluorophore. By using a capacitor to store electrical energy from the respective photodetectors in response to the fluorescent decay of the respective fluorophore, the amount electrical energy may more accurately represent the fluorescent decay compared to other methods, such as time dependent sampling of the fluorescence of the respective fluorophore. Additionally, or alternatively, using a capacitor to store electrical energy indicative of the fluorescent decay may simplify circuitry design relative to other methods, such as time dependent sampling of the fluorescence of the respective fluorophore.

Each of signal identification module 196 and signal analysis module 198 may be implemented in various ways. For example, one or more of signal identification module 196 and signal analysis module 198 may be implemented as an application or a part of an application executed by processing circuitry 104. In some examples, one or more of signal identification module 196 and signal analysis module 198 may be implemented as part of a hardware unit of medical device 100 (e.g., as circuitry). In some examples, one or more of signal identification module 196 and signal analysis module 198 may be implemented remotely on external device 12, for example, as part of an application executed by one or more processors of external device 12 or as a hardware unit of external device 12. Functions performed by one or more of signal identification module 196 and signal analysis module 198 are explained below with reference to the example flow diagram illustrated in FIG. 8.

Processing circuitry 104 may be configured to communicate, via antenna 106, with one or more external devices 24. For example, medical device 100 may include communications circuitry 190 operatively coupled to processing circuitry 104. Communications circuitry may be configured to send and receive signals to enable communication with an external device 12 via antenna 106. Communications circuitry 190 may include a communications interface, such as a radio frequency transmitter and/or receiver, cellular transmitter and/or receiver, a Bluetooth® interface card, or any other type of device that can send information or send and receive information. In some examples, the communications interface of communications circuitry 190 may be configured to send and/or receive data via antenna 106. In some examples, medical device 100 uses communications circuitry 190 to wirelessly transmit (e.g., a one-way communication) data to external device 12. In some examples, external devices 24 may include, but is not limited to, a radio frequency identification reader, a mobile device, such as a cell phone or tablet, or a computing device operatively coupled to an electronic medical records database or remote server system. In this way, antenna 106 may be operatively coupled to the processing circuitry and configured to transmit data representative of the concentration of the analyte to external device 12.

Medical device 100 includes antenna 106 operatively coupled to processing circuitry 104 to enable medical device 100 to communicate to external device 12 (FIG. 1A), e.g., while operating completely within a biological system. In some examples, processing circuitry 104 may cause communication circuitry 190 to transmit, via antenna 106, data indicative of a determined concentration of an analyte, such as processed data, unprocessed signals from optical sensor 184, or both. In some examples, external device 12 may continuously or periodically interrogate or poll communications circuitry 190 via antenna 106 to cause processing circuitry 104 to receive, identify, or process signals from optical sensor 184. By receiving, identifying, or processing signals from optical sensor 184 only when interrogated or polled by external device 12, processing circuitry may conserve power or processing resources. In some examples, medical device 100 may be configured to enable chronic, continuous, and/or substantially continuous monitoring of the analyte concentration in the biological system.

Medical device 100 includes housing 110 that is configured to protect components of medical device 100 from the environment of the biological system. Housing 110 may be formed to separate at least a portion of one or more of optical sensor 102, processing circuitry 104, and/or an antenna 106 from the environment surrounding medical device 100. In some examples, housing 110 may include one or more biocompatible materials coating or encasing the components of medical device 100. One or more components of medical device 100, such as portions of optical sensor 102 may be disposed outside housing 110, such as, for example, affixed to an external surface of housing 110 or defining an external surface of medical device 100. As one example, antenna 106 may be affixed to an external surface of housing 110 to improve transmission properties of antenna 106. Housing 110 may include any suitable shape, such as rectilinear or curvilinear. In some examples, housing 110 may be shaped to facilitate insertion of medical device 100 into a body cavity of a human patient. For example, housing 110 may include a cylindrical shape to be loaded into an insertion tool or include rounded corners and edges to reduce irritation to the patient.

Housing 110 may be any suitable dimensions. In some examples, a height of housing 110 may be between approximately 1 millimeter (mm) and approximately 8 mm, such as approximately 4 mm. In some examples, a width of housing 110 may be between approximately 5 mm and approximately 15 mm, such as approximately 7 mm. In some examples, a length of the housing 182 may be between approximately 20 mm and approximately 60 mm, such as approximately 45 mm. In some examples, the components of medical device 100 may be layered or stacked inside housing 110 to reduce the size of medical device 100 compared to a device in which the components are not layered or stacked.

Medical device 100 includes sensing circuitry 130, for example, to generate sensor data from sensor signals received from sensor(s) that encode patient physiological parameters. Sensing circuitry 130 and processing circuitry 104 may store the sensor data as a portion of patient data in storage components 188. Sensing circuitry 130 may be selectively coupled to electrodes via switching circuitry, e.g., to sense electrical signals of the heart of patient, for example by selecting the electrodes and polarity, referred to as the sensing vector, used to sense a cardiac EGM, as controlled by processing circuitry 104. Sensing circuitry 130 may sense signals from electrodes 16, e.g., to produce an internal cardiac electrogram (EGM)), in order to facilitate monitoring the electrical activity of the heart. Sensing circuitry 130 may monitor signals from sensors, such as motion sensors 120, which may include one or more accelerometers; other sensors include pressure sensors, and/or optical sensors, as examples. In some examples, sensing circuitry 130 may include one or more filters and amplifiers for filtering and amplifying signals received from the electrodes and/or the sensors. Sensing circuitry 130 may capture signals from any one of sensors, e.g., to produce patient data, in order to facilitate monitoring the electrical activity of the heart and detecting changes in patient health.

FIG. 1C is a conceptual diagram of an example medical system 10A in conjunction with a patient 2, in accordance with one or more techniques of this disclosure. Medical device 100A of medical system 10A may be implanted or inserted subcutaneously under a scalp or on a cranium of the human patient. Medical system 10A may be substantially similar to medical system 10 of FIG. 1A where medical device 100 may be implanted or inserted in a pectoral region. However, medical device 100A of medical system 10A may be configured to be implanted in target region 17, which is located at a rear portion of the neck or the base of the skull of patient 2.

In the illustrated example, medical device 100A of medical system 10A includes a housing that carries three electrodes 16 (one of which is labeled in FIG. 1D). Although three electrodes are shown for medical device 100A of medical system 10A, in other examples, two or four or more electrodes may be carried by the housing of medical device 100A of medical system 10A. As illustrated, the housing of medical device 100A can define a boomerang or chevron-like shape, which a central portion includes a vertex, with lateral portions extending laterally outward and from the central portion and also at a downward angle with respect to a horizontal axis of medical device 100A. In other examples, the housing of medical device 100A may be formed in other shapes, which may be determined by desired distances or angles between different electrodes carried by the housing. The configuration of the housing can facilitate placement either over the skin of patient 2 in a wearable or bandage-like form or for subcutaneous implantation. As such, a relatively thin housing can be advantageous. Additionally, the housing of medical device 100A can be flexible in some embodiments, so that the housing can at least partially bend to correspond to the anatomy of the neck of patient 2 (e.g., with left and right lateral portions of the housing of medical device 100A bending anteriorly relative to the central portion of the housing of medical device 100A).

Medical device 102A implanted on the upper arm of patient 2 may be configured (e.g., as a glucose sensor) to sense detect blood glucose concentration or changes in blood glucose concentration, as well as other sensor signals described herein, in this area. For example, medical device 102A may include one or more optical hematocrit sensor and may be configured to detect the change with the circulating blood volume. In other examples, medical device 102A may be configured to sense signals as described herein from other areas of patient 2 that may be outside of the upper arm of patient 2.

FIG. 1D is a conceptual diagram of an example medical system 10B in conjunction with a patient 2, in accordance with one or more techniques of this disclosure. Medical system 10B may be substantially similar to medical system 10A of FIG. 1C. However, as an alternative or in addition to electrodes 16 on its housing, medical device 100B of medical system 10B further include electrode extensions 19 (one of which is labeled in FIG. 1D) including electrodes 16. As illustrated in FIG. 1D, electrode extensions 19 of medical device 100B include paddles such that one or more electrodes 16 are distributed on the paddles. In some examples, electrode extensions 19 of medical device 100B include one or more ring electrodes. In some examples, electrode extensions 19 of medical device 100B may be connected to the housing of medical device 100C via header pins. In some examples, electrode extensions 19 of medical device 100B may be permanently attached to the housing of medical device 100B.

In the example of FIG. 1D, medical device 102B is implanted on the abdomen of patient 2 and may be configured to sense detect blood glucose concentration or changes in blood glucose concentration, as well as other sensor signals described herein, in this area. For example, medical device 102B may include one or more optical hematocrit sensor and may be configured to detect the change with the circulating blood volume. In other examples, medical device 102B may be configured to sense signals as described herein from other areas of patient 2 that may be outside of the abdomen of patient 2.

Figure 2:
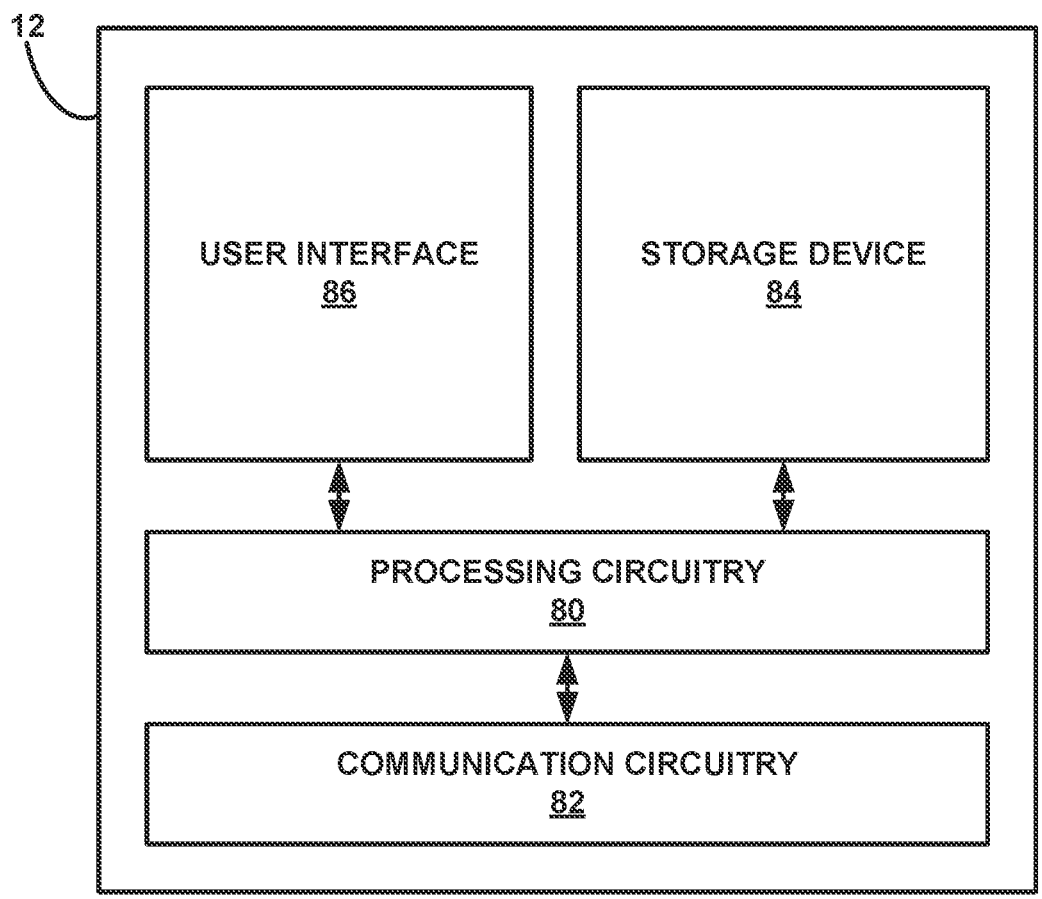
FIG. 2 is a functional block diagram illustrating an example configuration of the external device of FIG. 1, in accordance with one or more examples of the present disclosure.

FIG. 2 is a block diagram illustrating an example configuration of components of external device 12. In the example of FIG. 2, external device 12 includes processing circuitry 80, communication circuitry 82, storage device 84, and user interface 86.

Processing circuitry 80 may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, a cardiac monitor and/or a glucose monitor, such as medical device 100 or another device. Communication circuitry 82 may be configured to transmit or receive signals via inductive coupling, electromagnetic coupling, NFC, RF communication, Bluetooth, WiFi, or other proprietary or non-proprietary wireless communication schemes. Communication circuitry 82 may also be configured to communicate with devices other than medical device 100 via any of a variety of forms of wired and/or wireless communication and/or network protocols.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and medical device 100 may include operational parameters. External device 12 may transmit data including computer readable instructions which, when implemented by medical device 100, may control medical device 100 to change one or more operational parameters and/or export collected data. For example, processing circuitry 80 may transmit an instruction to medical device 100 which requests medical device 100 to export collected data to external device 12. In turn, external device 12 may receive the collected data from medical device 100 and store the collected data in storage device 84. The data external device 12 receives from medical device 100 may include metadata (e.g., timestamps, message header attributes, and/or the like), control data (e.g., operational parameters), patient data (e.g., patient data 6 of FIG. 1) including physiological parameters, episode data (e.g., cardiac EGMs), patient activity data, and other patient information. Processing circuitry 80 may implement any of the techniques described herein to analyze the data from medical device 100 to determine input feature values for a machine learning model as described herein. The input feature values may be based on raw data (e.g., sensor data such as continuous glucose measurements and event data such as counts of hyperglycemic and hypoglycemic events), processed data (e.g., metric values such as healthy and unhealthy glucose range times and statistics for the raw data such as a standard deviation) and any other data with insight into determining whether the patient is experiencing a change in health e.g., a cardiovascular event, based upon one or more criteria.

A user, such as a clinician or patient 2, may interact with external device 12 through user interface 86. User interface 86 includes a display (not shown), such as a liquid crystal display (LCD) or a light emitting diode (LED) display or other type of screen, with which processing circuitry 80 may present information related to medical device 100, e.g., predications of the machine learning model and indications of changes in patient health that correlate to the predications of the machine learning model as well as detections (e.g., initial detections) of cardiac episodes and other episode data, such as cardiac EGM (e.g., electrocardiogram (ECG)) waveforms. In addition, user interface 86 may include an input mechanism configured to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to the user, receiving voice commands from the user, or both.

Figure 3:
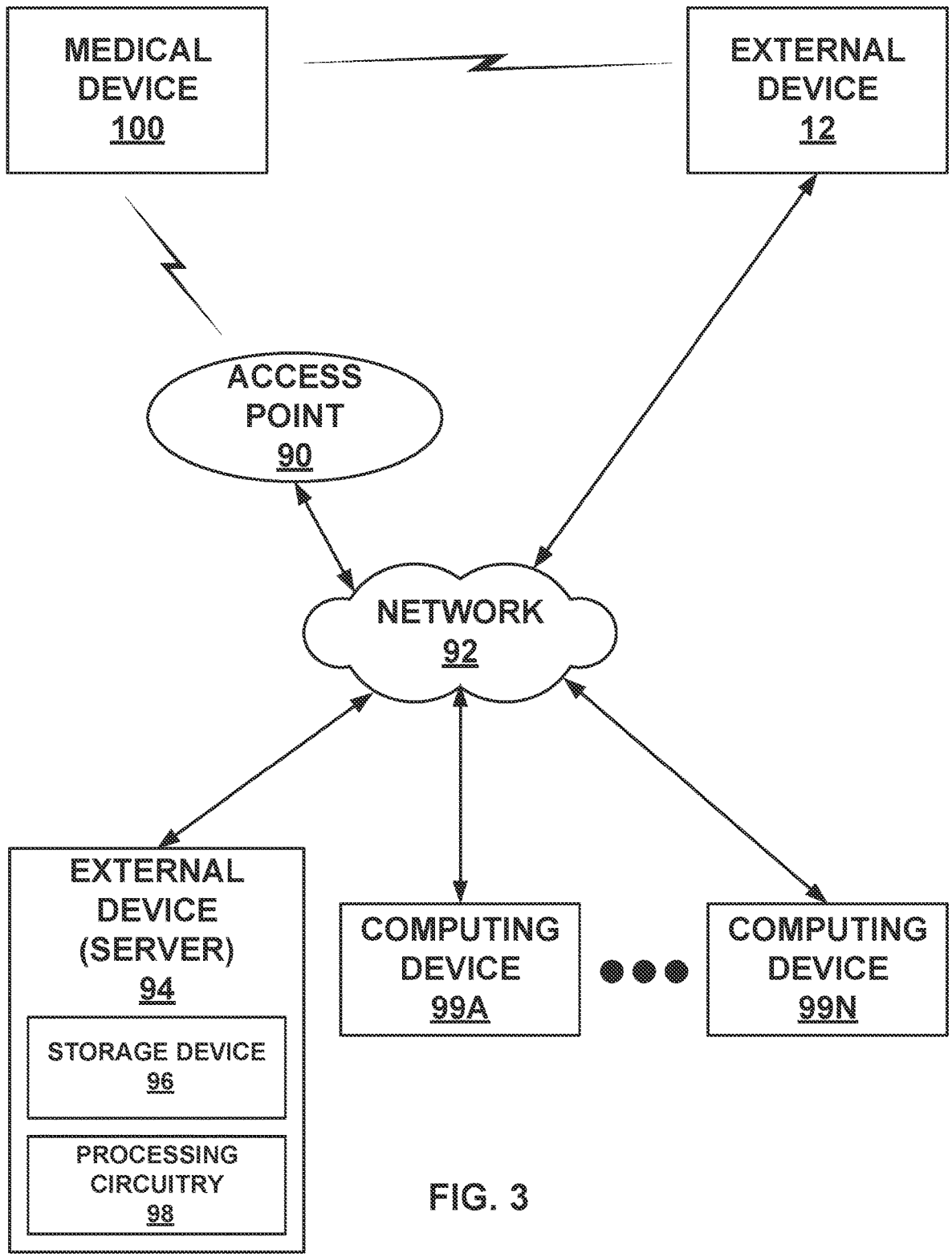
FIG. 3 is a block diagram illustrating an example system that includes an access point, a network, external computing devices, such as a server, and one or more other computing devices, which may be coupled to the medical device and external device of FIGS. 1-2, in accordance with one or more examples of the present disclosure.
Figure 5:
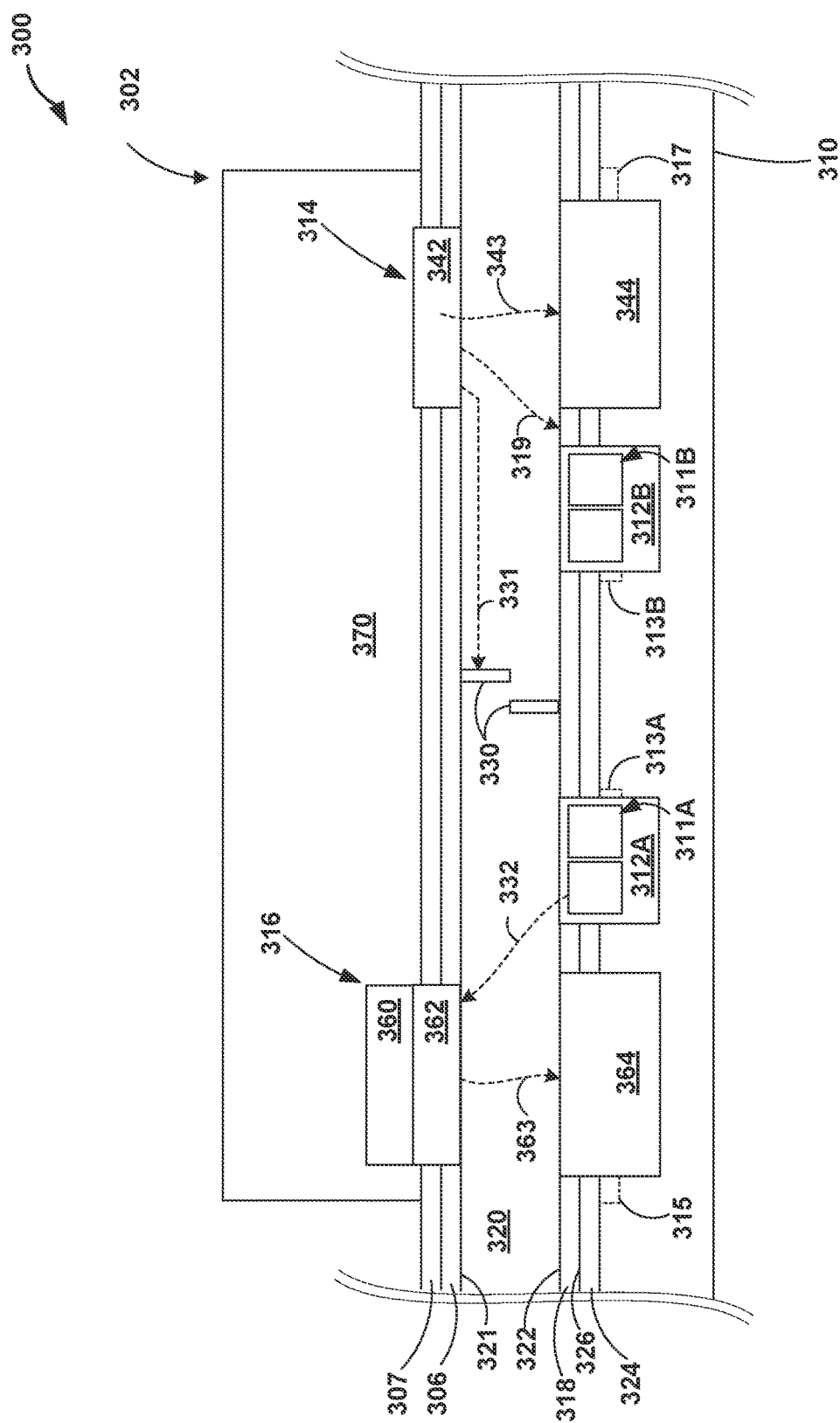
FIG. 5 is a conceptual diagram illustrating a partial cross-sectional side view of an example medical device including an optical sensor.

FIG. 3 is a block diagram illustrating an example system that includes an access point 90, a network 92, external computing devices, such as a server 94, and one or more other computing devices 99A-99N (collectively, "computing devices 99"), which may be coupled to medical device 100 and external device 12 via network 92, in accordance with one or more techniques described herein. In this example, medical device 100 may use communication circuitry 54 to communicate with external device 12 via a first wireless connection, and to communicate with an access point 90 via a second wireless connection. In the example of FIG. 5, access point 90, external device 12, server 94, and computing devices 99 are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. Medical device 100 may be configured to transmit data, such as a patient's raw or processed collected data, to access point 90 for storage in storage device 96 (e.g., as patient data 6 of FIG. 1A). Access point 90 may then communicate the retrieved data to server 94 via network 92. As described herein, examples of such patient data include sensor measurements (e.g., glucose sensor measurements), events (e.g., hypoglycemic or hyperglycemic events), metric values (e.g., physiological parameters), episode data, electrocardiogram, and/or indications of changes in patient 2's health.

In some cases, server 94 may be configured to provide a secure storage site for data that has been collected from medical device 100 and/or external device 12. In some cases, server 94 may assemble data in web pages or other documents for viewing by trained professionals, such as clinicians, via computing devices 99. One or more aspects of the illustrated system of FIG. 5 may be implemented with general network technology and functionality, which may be similar to that provided by the Medtronic CareLink® Network.

In some examples, one or more of computing devices 99 may be a tablet or other smart device located with a clinician, by which the clinician may program, receive alerts from, and/or interrogate medical device 100. For example, the clinician may access data such as the above-mentioned patient data and/or indications of patient health collected by medical device 100 through a computing device 99, such as when patient 2 is in in between clinician visits, to check on a status of a medical condition. In some examples, the clinician may enter instructions for a medical intervention for patient 2 into an application executed by computing device 99, such as based on a status of a patient condition determined by IMD 10, external device 12, server 94, or any combination thereof, or based on other patient data known to the clinician. Device 99 then may transmit the instructions for medical intervention to another of computing devices 99 located with patient 2 or a caregiver of patient 2. For example, such instructions for medical intervention may include an instruction to change a drug dosage, timing, or selection, to schedule a visit with the clinician, or to seek medical attention. In further examples, a computing device 99 may generate an alert to patient 2 based on a status of a medical condition of patient 2, which may enable patient 2 proactively to seek medical attention prior to receiving instructions for a medical intervention. In this manner, patient 2 may be empowered to take action, as needed, to address his or her medical status, which may help improve clinical outcomes for patient 2.

In the example illustrated by FIG. 3, server 94 includes a storage device 96, e.g., to store data retrieved from IMD 10, and processing circuitry 98. Although not illustrated in FIG. 5 computing devices 99 may similarly include a storage device and processing circuitry. Processing circuitry 98 may include one or more processors that are configured to implement functionality and/or process instructions for execution within server 94. For example, processing circuitry 98 may be capable of processing instructions stored in storage device 96. Processing circuitry 98 may include, for example, microprocessors, DSPs, ASICs, FPGAs, or equivalent discrete or integrated logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98. Processing circuitry 98 of server 94 and/or the processing circuitry of computing devices 99 may implement any of the techniques described herein to analyze information received from medical device 100, e.g., to determine whether the health status of a patient has changed, for example, based on the patient's risk level of having a cardiovascular event.

Storage device 96 may include a computer-readable storage medium or computer-readable storage device. In some examples, storage device 96 includes one or more of a short-term memory or a long-term memory. Storage device 96 may include, for example, RAM, DRAM, SRAM, magnetic discs, optical discs, flash memories, or forms of EPROM or EEPROM. In some examples, storage device 96 is used to store data indicative of instructions for execution by processing circuitry 98.

Figure 4:
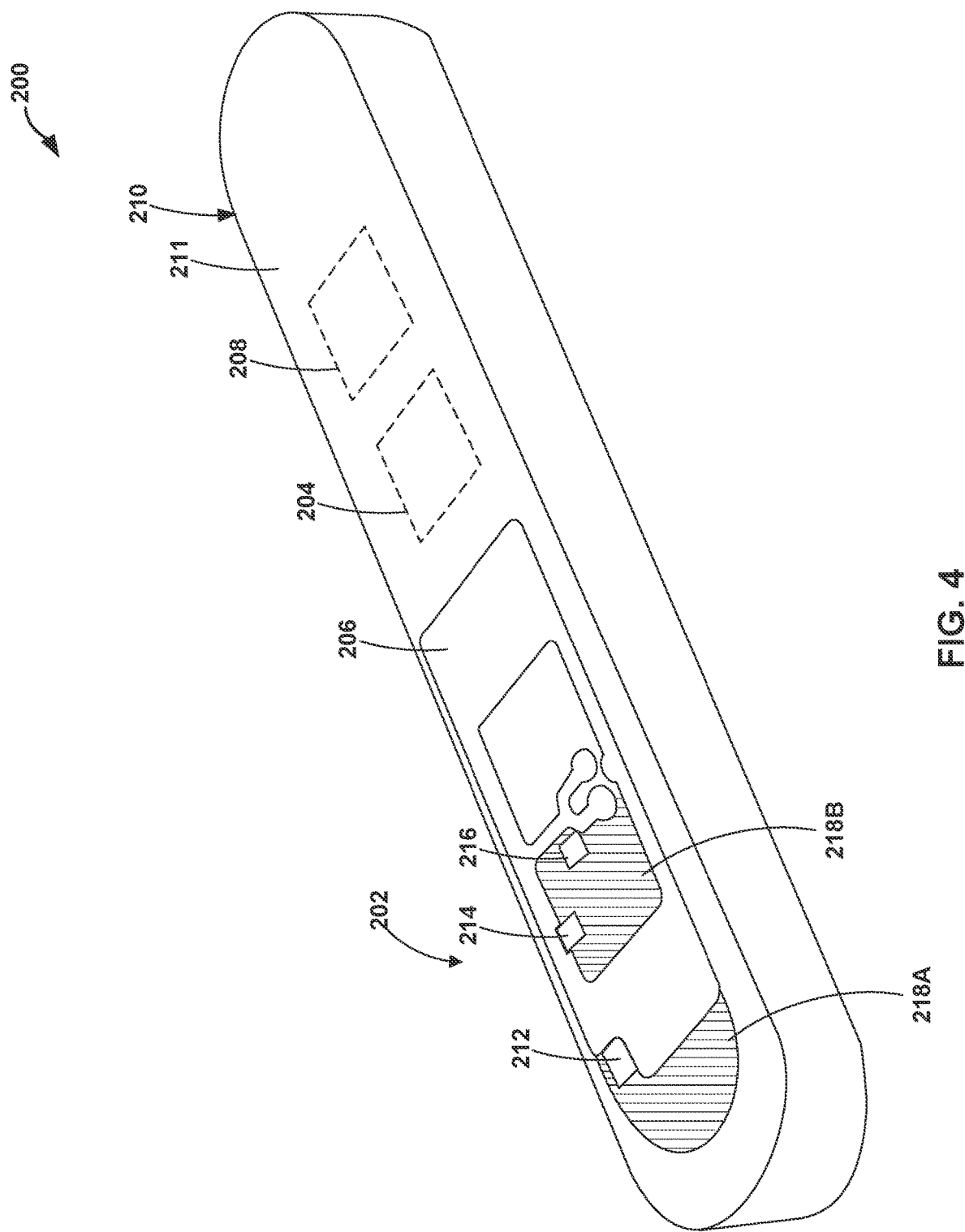
FIG. 4 is a conceptual diagram illustrating a perspective view of an example medical device including an optical sensor.

In some examples, the components of medical device 100 may be arranged to facilitate operation of the components. FIG. 4 is a conceptual diagram illustrating a perspective view of an example medical device 200 including an optical sensor 202. Medical device 200 may be the same or substantially similar to medical device 100 discussed above in reference to FIG. 1. For example, medical device 200 may include optical sensor 202 including light source 212, reference optical beacon 214, and test optical beacon 216, processing circuitry 204, antenna 206, power source 208, and housing 210, which may be the same or substantially similar to the similarly numbered features discussed above in reference to medical device 100 illustrated in FIGS. 1A and 1B. Although not illustrated in FIG. 4, medical device 200 may include electrodes, e.g. for sensing a cardiac EGM, impedance, and/or other parameters of patient 2, as described above with respect to FIGS. 1A and 1B.

As illustrated in FIG. 4, antenna 206 is disposed on an exterior surface 211 of housing 210. In some examples, antenna 206 may include a substrate layer and a metalized layer formed on the substrate layer. The substrate layer may include, for example, biocompatible polymer, such as polyamide or polyimide, silica glass, silicon, sapphire, or the like. The metalized layer may include, for example, aluminum, copper, silver, or other conductive metals. Antenna 206 may include other materials, such as, for example, ceramics or other dielectrics (e.g., as in dielectric resonator antennas). In some examples, antenna 206, e.g., a metalized layer or the like, may be formed directly on exterior surface 211 of housing 210.

Regardless of the material, antenna 206 may include an opaque or substantially opaque material. For example, an opaque (e.g., or substantially opaque) material may block transmission of at least a portion of radiation of a selected wavelength, such as, between about 75% and about 100% of visible light.

In examples in which antenna 206 includes an opaque material, components of optical sensor 202 may be arranged relative to portions of antenna 206 to reduce or prevent optical interference between components. For example, as illustrated in FIG. 2, light source 212 is positioned on an outer perimeter of antenna 206, whereas reference optical beacon 214 and test optical beacons 216 are positioned within an aperture defined by antenna 206. In this way, antenna 206 may define an optical boundary of opaque material that reduces or prevents transmission of light from light source directly to a respective photodetector of reference optical beacon 214 and test optical beacons 216. Rather, light emitted from light source 212 must travel through an environment external to medical device 200. In this way, the emitted light may be incident only on the fluorophore of reference optical beacon 214 and the fluorophore and/or reactive substrate of test optical beacon 216. Hence, the optical signal generated by the respective photodetector of reference optical beacon 214 and test optical beacon 216 is produced substantially only by fluorescence of the respective fluorophores. Being produced substantially only by fluorescence of the respective fluorophores may exclude ambient radiation, fluorescence emitted by adjacent fluorophores, or light transmitted from light source 212 through components (e.g., a substrate) of medical device 200 to the respective photodetectors.

Although not illustrated in FIG. 2, in some examples, reference optical beacon 214 and test optical beacon 216 may be disposed on opposing portions of antenna 206. Disposing reference optical beacon 214 and test optical beacon 216 on opposing portions of antenna 206 may reduce or prevent fluorescence emitted by a respective fluorophore of reference optical beacon 214 and test optical beacon 216 from being detected by the respective photodetector of the other of reference optical beacon 214 and test optical beacon 216.

Additionally, or alternatively, medical device 200 may include optional optical masks 218A and 218B (collectively, optical mask 218). Optical mask 218 may be configured to reduce or prevent transmission of radiation out of or into a substrate of medical device 200. For example, as discussed above in reference to FIG. 1, a substrate of medical device 200 may include one or more transparent (e.g., or semi-transparent) materials, such as glass or sapphire. Portions of optical sensor 202, such as light source 212 and/or respective photodetectors of reference optical beacon 214 and test optical beacon 216 may be disposed within (e.g., under) the transparent material, relative to the environment surrounding medical device 200.

Light emitted from light source 112 may travel through the transparent material into the environment surrounding medical device 200. In some examples, at least a portion of the light may be incident on the transparent material at an angle that causes reflection or total internal reflection of the portion of light. Additionally, or alternatively, in examples in which medical device 200 is implanted in a patient, the tissue or biological material surrounding medical device 200 may cause diffuse scattering of the light. At least a portion of the scattered light may be incident on the transparent material at an angle causing total internal reflection of the portion of scattered light. Optical mask 218 may be disposed on an interior surface and/or an exterior surface of the transparent material to reduce or prevent reflection and/or total internal reflection of the light. In this way, optical mask 218 may reduce or prevent stray light from being transmitted through the transparent substrate to respective photodetectors of reference optical beacon 114 and test optical beacon 116.

The optional optical mask 218 may include a material configured to substantially absorb radiation emitted by light source 212. In some examples, optical mask 218 may include titanium nitride, columnar titanium nitride, titanium, or another material suitable to absorb selected wavelengths of radiation that may be emitted by light source 212.

FIG. 5 is a conceptual diagram illustrating a partial cross-sectional side view of an example medical device 300 including an optical sensor 302. Medical device 300 may be the same or substantially similar to medical device 100 and/or medical device 200 discussed above in reference to FIGS. 1 and 2. For example, optical sensor 302 may include light sources 312A and 312B (collectively, light sources 312), reference optical beacon 314, test optical beacon 316, and antenna 306, and may be optatively coupled to processing circuitry and a power source (not illustrated), and may be encased in housing 310, which may be the same or substantially similar to the similarly numbered features discussed above in reference to medical device 100 and/or medical device 200 illustrated in FIGS. 1A, 1B, and 2.

Optical sensor 302 may include any suitable arrangement of light sources 312, reference optical beacon 314, and test optical beacon 316. As illustrated in FIG. 3, medical device 300 includes a substrate layer 320 defining surfaces 321 and 322. In some examples, substrate layer 320 may include sapphire, a sapphire wafer, silica glass, a glass wafer, silicon, a biocompatible polymer, polyamide, polyimide, a liquid crystal polymer, or a dielectric material. In some examples, surfaces 321 and/or 322 are substantially planar. In other examples, surfaces 321 and/or 322 may define surface features, such as ridges, valleys, or apertures, corresponding to features such as at least a portion of light sources 312, reference optical beacon 314, and test optical beacon 316, electrical traces, through vias, light blocking regions, or the like. Surface features on or in surfaces 321 and/or 322 may be formed by any suitable means, such as, for example, machining, laser etching, chemical etching, or semiconductor manufacturing techniques such as front-end-of-line (FEOL) processes. In this way, substrate layer 320 may be formed to support additional layers, facilitate manufacture of the medical device 300, or both.

An optical mask 318 may be disposed on at least a portion of surface 322 or, in some examples, a portion of surface 321. As discussed above in reference to FIG. 2, optical mask 318 is configured to reduce or prevent transmission of radiation out of or into substrate layer 320 of medical device 200. For example, optical mask 318 may absorb radiation, such as light ray 319, incident on optical mask 318.

An interconnect layer 324 may be disposed on surface 326 of optical mask 318. Interconnect layer 324 is configured to electrically couple light sources 312, reference optical beacon 314, and test optical beacon 316 to processing circuitry and/or a power source of medical device 300. For example, light sources 312, reference optical beacon 314, and test optical beacon 316 may be electrically coupled to interconnect layer 324 by respective electrical traces 313A, 313B, 315, and 317.

Interconnect layer 324 may include an electrically conductive material, such as, for example, aluminum, cadmium, chromium, copper, gold, nickel, platinum, titanium, indium nitride, indium phosphide, zinc oxide, alloys thereof, or the like. In some examples, surface 322 may be metallized by, for example, chemical vapor deposition, physical vapor deposition, thermal spraying, cold spraying, or the like, to form interconnect layer 324. In some examples, interconnect layer 324 may form a plurality of electrical traces, e.g., formed using semiconductor manufacturing techniques such as back-end-of-line (BEOL) processes. A respective electrical trace or the plurality of electrical traces may electrically couple one or more components of medical device 300.

Although illustrated as embedded or partially embedded in optical mask 318 and interconnect layer 324, in some examples, one or more portions of light sources 312, reference optical beacon 314, and test optical beacon 316 may be formed on a portion of optical mask 318 and/or interconnect layer 324. For example, light sources 312 may be positioned on and electrically coupled to a surface of optical mask 318 and/or interconnect layer 324, where optical mask 318 and interconnect layer 324 may define an aperture optically coupling light sources 312 to substrate 320. Each of reference optical beacon 314 and test optical beacon 316 may be similarly positioned on a surface of optical mask 318 and/or interconnect layer 324.

In some examples, medical device 300 may include one or more optical barriers 330 extending at least partially through substrate layer 320. For example, optical barrier 330 may extend through at least a portion of substrate layer 320. Optical barriers 330 may extend through only a portion of substrate layer 320 to enable substate layer 320 to define a hermetic seal between an interior and exterior of medical device 300. Optical barrier 330 may be substantially the same as or similar to optical mask 318, except that optical barrier 330 may extend into substrate layer 320. For example, optical barrier 330 may include a material configured to absorb at least a portion of radiation transmitted through substrate layer 320. In some examples, radiation, such as light ray 331, may be incident on an interface between fluorophore 324 and substrate layer 320 at an angle that results in total internal reflection of the radiation. By orienting optical barrier 330 between components of optical sensor 302, optical barrier may substantially reduce or prevent light ray 331 from reaching photodetector 364 of test optical beacon 316. In this way, one or more optical barriers 330 may be disposed between reference optical beacon 314 and test optical beacon 316 to reduce or prevent fluorescence emitted from either reference optical beacon 314 and test optical beacon 316 from reaching the other of reference optical beacon 314 and test optical beacon 316.

In operation, when light is emitted from light source 312A, e.g., by LEDs 311A, the light, e.g., light ray 332, may travel through a portion of substrate layer 320 and may be incident on test optical beacon 316. When light is emitted from light source 312B, e.g., by LEDs 311B, the light may travel through a portion of substrate layer 320 and may be incident on test optical beacon 314.

Reference optical beacon 314 includes a fluorophore 342 and a photodetector 344. At least a portion of radiation emitted by light source 312B is incident on fluorophore 342. Fluorophore 342 absorbs at least a portion of the radiation, and emits a fluorescence 343 that is incident on photodetector 344. Fluorophore 342 is exposed to the environment surrounding medical device 300. In some examples, as discussed above, the fluorescence 343 of fluorophore 342 in response to incident radiation is associated with a concentration of substance present in the environment surrounding medical device 300. For example, fluorescence 343 may be quenched, e.g., reduced, proportional to a concentration of oxygen proximate fluorophore 342.

Test optical beacon 316 includes a reagent substrate 360, a fluorophore 362, and a photodetector 364. At least a portion of radiation, e.g., light ray 332, emitted by light source 312A is incident on fluorophore 362. Fluorophore 362 absorbs at least a portion of the incident radiation, and emits a fluorescence 363 that is incident on photodetector 364. Fluorophore 362 is exposed to reagent substrate 360. Reagent substrate 360, and in some examples at least a portion of fluorophore 362, is exposed to the environment surrounding medical device 300. Although illustrated as distinct layers, in some examples, reagent substrate 360 and fluorophore 362 may define a single layer, such as a layer composing a homogeneous mixture, heterogeneous mixture, or composite of reagent substrate 360 and fluorophore 362.

As discussed above in reference to FIG. 1, reagent substrate 360 may be configured to react with an analyte present in the proximate environment to modulate the concentration of the substance that interacts with fluorophore 362. In some examples, reagent substrate 360 includes an immobilization substrate configured to immobilize a reagent. As discussed above, the reagent may include at least one enzyme, catalyst, or other material configured to react with the analyte to yield the substance. In examples in which the analyte includes glucose and the substance includes oxygen, the reagent may include an oxidase enzyme, such as glucose oxidase. In some examples, the reagent may be immobilized on an immobilization substrate by, for example, physical entrapment (e.g., a respective reagent physically unable to pass through pores of the immobilization substrate), chemical bonding (e.g., ionic bonding, covalent bonding, van der Waals forces, and the like), or combinations thereof. In some examples, the immobilization substrate may include a polymer, such as polylysine, aminosilane, epoxysilane, or nitrocellulose, or a substrate having a three-dimensional lattice structure, such as a hydrogel, an organogel, or a xerogel. In some examples, the immobilization substrate may include a ligand configured to chemically bond to at least a portion of a respective reagent. For example, the immobilization substrate including glutaraldehyde may immobilize glucose oxidase. A respective immobilization substrate including primary amine conjugation enniatin may immobilize (used for sodium Na+ detection) can be immobilized to the working electrode through. In some examples, the immobilization substrate may include, but is not limited to, glutaraldehyde, thiol based conjugation compounds (e.g., 16-mercaptohexadecanoic acid (MHDA), diethyldithiocarbamic acid (DSH), dithiobissuccinimidylundecanoate (DSU), purine conjugation compounds, streptavidin-biotin conjugation compounds, a primary amine and a vinyl pyridine polymer, lysine, 1-ethyl-3-(3-dimethylaminopropyl)carbodiimide hydrochloride (EDC) and N-hydroxysuccinimide (NHS) coupling, agarose based gel and polymer mixtures, silane crosslinker, (hydroxyethyl)methacrylate, and poly(ethylene glycol) diacrylate polymer. In some examples, the immobilization substrate may be transparent or semi-transparent to enable radiation, e.g., light rays 332B, to reach fluorophore 362. By immobilizing a reagent, the immobilization substrate may reduce loss of the reagent to the sample fluid.

In examples in which reagent substrate 360 includes at least one enzyme, the at least one enzyme may be selected based on the analyte to be detected. For example, the at least one enzyme may be selected from the group consisting of glucose oxidase, lactate oxidase, catalase, or mixtures thereof. In some examples, the at least one enzyme may be selected to react with a selected analyte and provide a reaction pathway to enable detection of the concentration of the selected analyte. For example, fluorescence 343 may be quenched, e.g., reduced, proportional to a concentration of oxygen proximate fluorophore 342. In examples in which reagent substrate 360 includes glucose oxidase (e.g., notatin), glucose oxidase may oxidize glucose in the sample fluid to produce D-glucono-δ-lactone and hydrogen peroxide. The hydrogen peroxide may be reduced by catalase to produce oxygen. This modulation in the oxygen concentration may be indicative of the glucose concentration in the sample fluid. In examples in which reagent substrate 360 includes lactate oxidase, lactate oxidase may oxidize lactic acid in the sample fluid to produce pyruvate and hydrogen peroxide. The hydrogen peroxide may be reduced by catalase to produce oxygen. This modulation in the oxygen concentration may be indicative of the lactic acid concentration in the sample fluid.

In some examples, reference optical beacon 314 and/or test optical beacon 316 may include one or more permeable membranes 370. Membrane 370 may be permeable to at least the analyte and, in some examples, configured to block interfering cellular bodies or molecules from binding or adhering to a respective constituents of reference optical beacon 314 and/or test optical beacon 316. For example, a glucose membrane may block large cellular bodies or molecules, such as red blood cells, white blood cells, acetaminophen, ascorbic acid, and the like. Membrane 370 may include, for example, one or more limiting membranes, one or more selective ion transfer membranes, one or more ionophore membranes, or combinations thereof. Limiting membranes may include, but are not limited to, polyurethane polyurea block copolymer including a mixture of materials, such as, e.g., hexamethylene, diisocyanate, aminopropyl-terminated siloxane polymer, and polyethylene glycol, or a vinyl pyridine-styrene copolymer mixed with epoxy groups and coated with polyethylene glycol. Selective ion transfer membranes may include a porous material having a net positive (or negative) charge to enabling permeation of ions having a like charge through the selective ion transfer membrane, while reducing permeation of ion having an opposite charge. Selective ion transfer membranes may include, but are not limited to, amino methylated polystyrene salicylaldehyde, dibenzo-18-crown-6, cezomycin, enniatin, gramicidin A, lasalocid, macrolides, monensin, narasin, nigericin, nigericin sodium salt, nonactin, polyimide/lycra blend, salinomycin, valinomycin, or mixtures thereof. Ionophore membranes may include a plurality of ionophores dispersed in an ionophore matrix material, where the plurality of ionophores may be selected to be preferentially permeable to a selected ion or group of ions. The ionophores may include, but are not limited to, crown ethers, cryptands, calixarenesm, phenols, amino methylated polystyrene salicylaldehyde, beauvericin, calcimycine, cezomycin, carbonyl cyanide m-chlorophenyl hydrazone, dibenzo-18-crown-6, enniatin, gramicidin A, ionomycin, lasalocid, macrolides, monensin, nigericin, nigericin sodium salt, narasin, nonactin, polyimide/lycra blend, salinomycin, tetronasin, valinomycin, potassium ionophore III (BME 44) or mixtures thereof. Ionophore matrix material may include, but is not limited to, polyvinylchloride, silicone, fluorosilicone, polyurethane, glutaraldehyde, UV curable polymers like PVA-SbQ, PVA hydrogels, pHEMA-HAA crosslinking, and agarose gel. In this way, the optical beacons may be configured to react with a selected analyte or a derivative thereof to produce a response signal to the presence of the selected analyte.

In some examples, one or more regions of membrane 370 may include a light absorbent material. For example, membrane 370 may include, in addition to the one or more above described limiting membranes, light absorptive material, a pigment, or a dye configured to at least partially absorb radiation incident on membrane 370. In some examples, the light absorbing region of membrane 370 may include a portion of membrane 370 disposed between optical beacons 314 and 316. In this way, membrane 370 may be configured to reduce transmission of radiation between fluorophores 342 and 362. Additionally, or alternatively, the light absorbing region of membrane 370 may include the entire volume or at least a total surface area of membrane 370. In this way, membrane 370 may substantially block ambient light incident on optical beacons 314 and 316.

Antenna 306 may be disposed on surface 321 of substrate layer 320. In some examples, antenna 306 may define an optical boundary of opaque material that reduces or prevents transmission of light between fluorophores 342 and 362 and/or between fluorophore 342 and photodetector 364 and/or between fluorophore 362 and photodetector 344.

Antenna may include any suitable material, such as, for example, titanium. or a titanium foil.

Electrode layer 307 may be disposed on antenna 306. Electrode layer 307 may define a conductive surface of medical device 300 that is configured to detect electrical signals within a human patient, such as, for example, cardiac EGM signals, as well as to make impedance measurements, e.g., for sensing perfusion or respiration of the patient. Electrode layer 307 may include any suitable material, such as, for example, titanium nitride.

Figure 6:
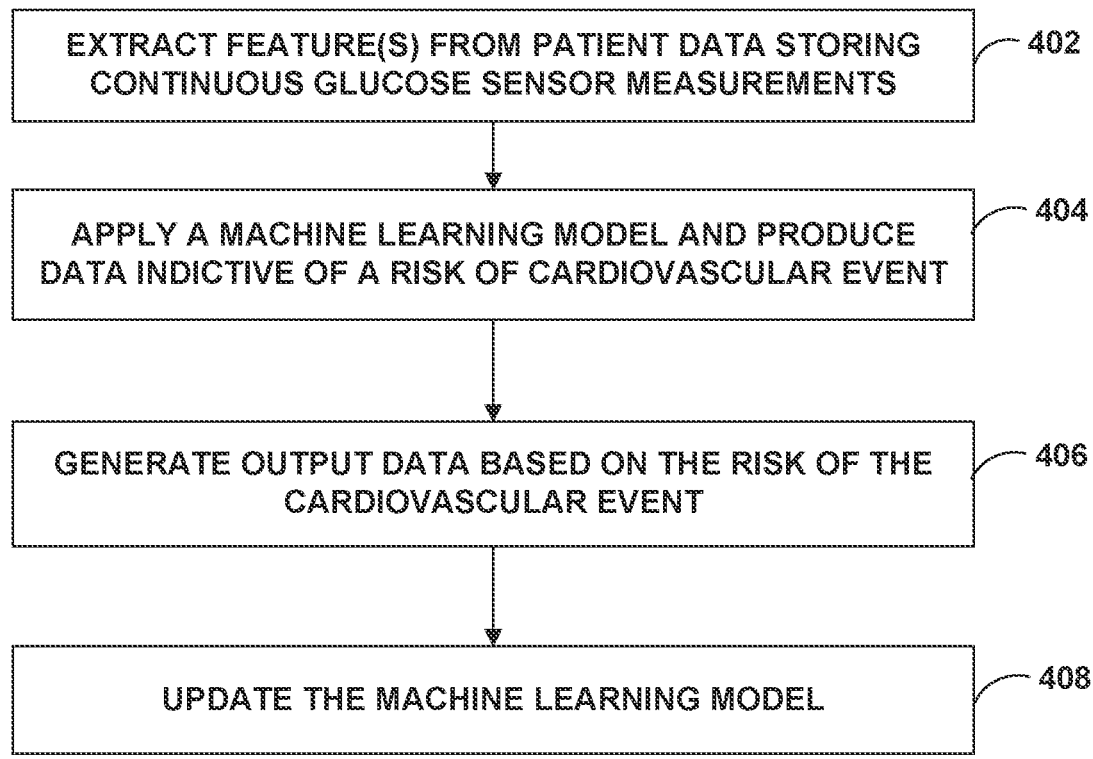
FIG. 6 is a flow diagram illustrating an example operation for using glucose sensor data to enable accurate detection of changes in patient health, in accordance with one or more examples of the present disclosure.

FIG. 6 is a flow diagram illustrating an example operation for determining changes in patient health or enabling accurate detection of changes in patient health, in accordance with one or more examples of the present disclosure. In some examples, the example operation may be implemented for determining whether a patient most likely has or is having a cardiovascular event of some type. As described herein, a machine learning model is configured to render a prediction/detection based on whether specific input features satisfy one or more prediction criteria and, in some instances, determining whether an initial detection by a medical device was false.

The following describes steps of FIG. 6 in reference to system 10 of FIGS. 1A-B. According to the illustrated example of FIG. 6, processing circuitry 80 of external device 12 monitors patient data provided by a cardiac monitor having a glucose sensor or a glucose monitor having a glucose sensor and extracts one or more features from such patient data storing continuous glucose sensor measurements (402). From the cardiac monitor or the glucose monitor, as discussed in greater detail with respect to FIGS. 1-2, processing circuitry 80 may receive raw sensor messages including the continuous glucose sensor measurements and processed data including events and metric values.

As further discussed herein, patient 2's glucose sensor measurements provide an accurate assessment of patient 2's cardiac health and his/her risk for (e.g., hospitalization due to) arrhythmia and/or stroke; hence, monitoring this patient's glucose levels provide an improved indication of changes in the patient's health and a reduced risk of stroke. The cardiac monitor or the glucose monitor may be implanted transcutaneously in interstitial fluid or a body cavity of patient 2 (as illustrated in FIG. 1A) or subcutaneously under a scalp or on a cranium of patient 2 (as illustrated in FIG. 1C and FIG. 1D). The cardiac monitor may also function as a neuro monitor to facilitate monitoring additional physiologic signals (e.g., cardiac electrogram (EGM), electroencephalogram (EEG) and activity/accelerometry) as depicted in FIG. 1C and FIG. 1D.

In the illustrated example, processing circuitry 80 of external device 12 applies a machine learning model to feature values and produce data indicative of a risk of cardiovascular event (404). In the example operation of FIG. 6, it is noted that there are a number of features that may be programmed as input (e.g., variables) into examples of a machine learning model defined in model data 8: one or more of an amount of time within a pre-determined glucose level range (e.g., range time), a number of hypoglycemia events (e.g., hypoglycemic event count), or a number of hyperglycemia events (e.g., hyperglycemic event count), statistical metrics corresponding to the continuous glucose sensor measurements, cardiac features, and/or the like. The amount of time within a pre-determined glucose level range includes an amount of time in a first (e.g., healthy) glucose range or a second (e.g., unhealthy) glucose range. Examples of the above statistical metrics include a standard deviation, a coefficient of variation, an average, a median, an interquartile range, a maximum rate of change of at least one dataset of the continuous glucose sensor measurements, and/or the like. The at least one dataset includes different time intervals of the continuous glucose sensor measurements. It should be noted that there are a number of other possible features that can be input for the machine learning model, such as at least one glucose sensor measurement feature and/or at least one cardiac feature to produce the data indicative of the risk of a cardiovascular event. Examples of cardiac features correspond to impedance and/or cardiac EGM metrics, including impedance, respiratory rate, night heart rate, heart rate variability, activity, or atrial fibrillation (AF) parameters.

Processing circuitry 80 of external device 12 generates output data based on the risk of the cardiovascular event (406). Based on the model's prediction, processing circuitry 80 generates output data corresponding to patient 2's cardiovascular risk level and/or whether that risk level is further indicative of some aspect (e.g., a risk of hospitalization) caused by the cardiovascular event (e.g., cardiac inflammation, heart failure, or an arrhythmia) and/or cardio-neurogenic event (e.g., ischemic and/or hemorrhagic stroke). External device 12 may include an electronic display operative to visually present the output data (e.g., in a user interface (UI)). In some examples, external device 12 generates and communicates, to medical device 100, the other medical device, or yet another device, output data indicative of patient 2's risk of at least one of cardiac inflammation, heart failure, or an arrhythmia. The device(s) receiving the output data may present such data and/or use the output data to perform some operation; for example, medical device 100 may use the risk level of the cardiovascular event to modify detection logic for the same cardiovascular event or another malady. As described herein, medical device 100 may implement a second machine learning model to predict an occurrence of a cardiovascular event or a diabetes-related condition. In another example, medical device 100 may receive a confirmation or rejection of medical device 100's initial detection of the cardiovascular event and use that confirmation or rejection to improve current detection logic.

In other examples, external device 12 computes a likelihood probability (e.g., a joint probability) that a glucose level (e.g., a recent/current measurement or a historical reading) of patient 2 causes any of the above-mentioned cardiovascular events. Processing circuitry 80 of external device 12 communicates that output data to a computing device over a network connection and/or returns the output data to patient 2's medical device. As described herein, the computing device is operated by a cardiac monitoring service, such as monitoring service 4 of FIG. 1A, and/or by patient 2 or patient 2's clinician.

Processing circuitry 80 of external device 12 updates the machine learning model (408). In some examples, processing circuitry 80 of external device 12 incorporates the above joint probability that patient 2's glucose level causes any of the above-mentioned cardiovascular events. The joint probability may be assumed to be a prior for one or more cardiovascular events. Further detail regarding the prediction of one or more cardiovascular events based on input features is provided herein for FIG. 7, which be included in the example operation illustrated in FIG. 6.

Figure 7:
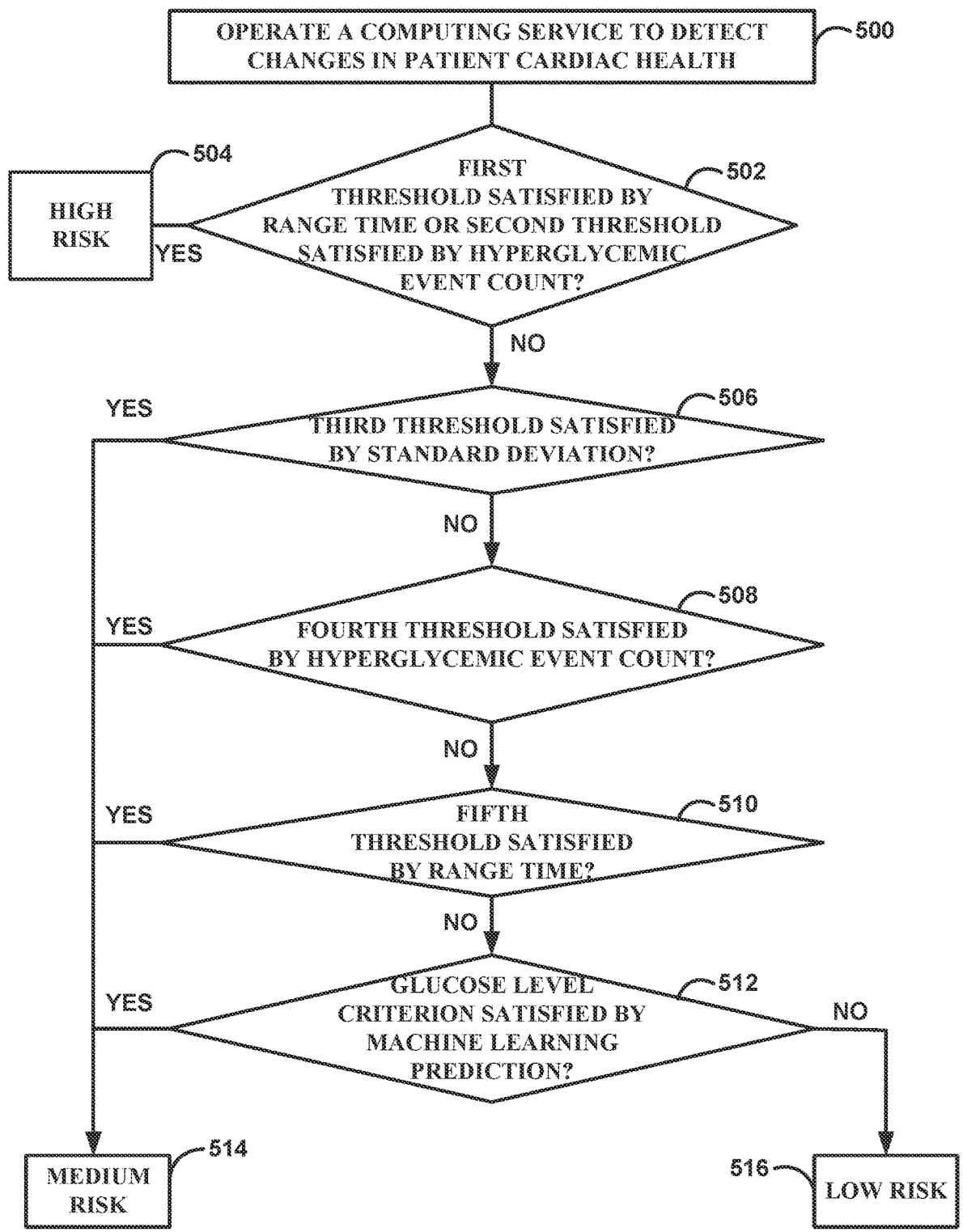
FIG. 7 is a flow diagram illustrating an example operation for detecting a change in patient health by an analysis of glucose sensor measurements, in accordance with one or more examples of the present disclosure.

FIG. 7 is a flow diagram illustrating an example operation for detecting a change in patient health based upon an evaluation by a machine learning model, in accordance with one or more examples of the present disclosure. According to FIGS. 1-6, monitoring service 4 runs a computing service on processing circuitry 80 of external device 12 to determine whether a given patient is currently at-risk for a cardiovascular event.

According to the illustrated example of FIG. 7, processing circuitry 80 of external device 12, on behalf of monitoring service 4, operates the computing service for patient 2 and detects changes in patient 2's cardiac health based on input feature values that are extracted from various data provided by medical device 100 (500). In particular, some (if not all) of patient 2's feature values corresponding to glucose sensor measurements generated by medical device 100 or another device having a glucose monitor and/or a cardiac monitor. A number of features may be configured as input features for a machine learning model defined by model data 8: one or more of an amount of time within a pre-determined glucose level range (e.g., range time), a number of hypoglycemia events (e.g., hypoglycemic event count), or a number of hyperglycemia events (e.g., hyperglycemic event count), statistical metrics corresponding to the continuous glucose sensor measurements, cardiac features, and/or the like. The amount of time within a pre-determined glucose level range includes an amount of time in a first (e.g., healthy) glucose range or a second (e.g., unhealthy) glucose range. Examples of the above statistical metrics include a standard deviation, a coefficient of variation, an average, a median, an interquartile range, a maximum rate of change of at least one dataset of the continuous glucose sensor measurements, and/or the like.

In the illustrated example of FIG. 7, after computing a range time as an amount of time within a pre-determined glucose level range and a hyperglycemic event count based on a number of such events within a time period, processing circuitry 80 of external device 12 compares the range time and the hyperglycemic event count with a first threshold and a second threshold (502). The first and second thresholds may be determined by training the machine learning model to predict a risk level that a patient, generally, and/or patient 2, specifically, has with respect to any of the cardiovascular events identified herein. In some examples, after comparing the above feature values with the first threshold and the second threshold, processing circuitry 80 of external device 12 determines whether the comparison satisfies either threshold. Based on a determination that one or both of the first threshold and the second threshold is/are satisfied (YES of 502), processing circuitry 80 of external device 12 generates output data indicative of a high risk of the cardiovascular event (504). Based on a determination that neither the first threshold nor the second threshold is satisfied (NO of 502), processing circuitry 80 of external device 12 computes a standard deviation of a dataset of glucose sensor measurements generated over the time period.

In the illustrated example of FIG. 7, after computing the standard deviation within the time period, processing circuitry 80 of external device 12 compares the standard deviation with a third threshold (506). Similar to the first and second thresholds, training the machine learning model using any known learning algorithm may set the third threshold to be a minimum or maximum value for the standard deviation of patient 2's glucose sensor measurements. In some examples, after comparing the above feature value with the third threshold, processing circuitry 80 of external device 12 determines whether the comparison satisfies that threshold. Based on a determination that the third threshold is satisfied (YES of 506), processing circuitry 80 of external device 12 generates output data indicative of a medium risk of the cardiovascular event (514). Based on a determination that the third threshold is not satisfied (NO of 506), processing circuitry 80 of external device 12 proceeds to evaluate patient 2's input feature values using additional criteria.

In the illustrated example of FIG. 7, processing circuitry 80 of external device 12 compares the hyperglycemic event count with a fourth threshold (508). In some examples, after comparing the above feature value with the fourth threshold, processing circuitry 80 of external device 12 determines whether the comparison satisfies that threshold. Based on a determination that the fourth threshold is satisfied (YES of 508), processing circuitry 80 of external device 12 generates output data indicative of a medium risk of the cardiovascular event (514). Based on a determination that the fourth threshold is not satisfied (NO of 508), processing circuitry 80 of external device 12 proceeds to evaluate patient 2's input feature values using additional criteria.

In the illustrated example of FIG. 7, processing circuitry 80 of external device 12 compares the range time with a fifth threshold (510). In some examples, after comparing the above range time with the fifth threshold, processing circuitry 80 of external device 12 determines whether the comparison satisfies that threshold. Based on a determination that the fifth threshold is satisfied (YES of 510), processing circuitry 80 of external device 12 generates output data indicative of a medium risk of the cardiovascular event (514). Based on a determination that the fifth threshold is not satisfied (NO of 510), processing circuitry 80 of external device 12 proceeds to compute one or more probabilities, each indicating a likelihood of that patient 2's glucose level measurements risk a cardiovascular event.

In the illustrated example of FIG. 7, after computing the likelihood probability based on measurements within the time period, processing circuitry 80 of external device 12 compares the likelihood probability with various criterion (512). In some examples, after comparing the likelihood probability with a threshold probability and other statistical metrics, processing circuitry 80 of external device 12 determines whether the comparison satisfies the various criterion. Based on a determination that the various criterion is/are satisfied (YES of 510), processing circuitry 80 of external device 12 generates output data indicative of a medium risk of the cardiovascular event (514). Based on a determination that the various criterion is/are not satisfied (NO of 508), processing circuitry 80 of external device 12 generates output data indicative of a low risk of the cardiovascular event for patient 2 (516).

The order and flow of the operation illustrated in FIGS. 6 and 7 are examples. In other examples according to this disclosure, more or fewer thresholds may be considered. Further, in some examples, processing circuitry may perform or not perform the methods of FIG. 6 and FIG. 7, or any of the techniques described herein, as directed by a user, e.g., via external device 12 or computing devices 99. For example, a patient, clinician, or other user may turn on or off functionality for identifying changes in patient health (e.g., using Wi-Fi or cellular services) or locally (e.g., using an application provided on a patient's cellular phone or using a medical device programmer).

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, FRAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Example 1: A method comprising: extracting at least one feature from continuous glucose sensor measurements of a patient over at least one time period, wherein the at least one feature comprises one or more of an amount of time within a pre-determined glucose level range, a number of hypoglycemia events, a number of hyperglycemia events, or one or more statistical metrics corresponding to the continuous glucose sensor measurements; applying a machine learning model to the at least one extracted feature to produce data indicative of a risk of a cardiovascular event; and generating an output based on the risk of the cardiovascular event.

Example 2: The method of example 1, wherein applying the machine learning model to the at least one extracted feature to produce data indicative of a risk of a cardiovascular event comprises applying the machine learning model to the at least one extracted feature to produce data indicative of a risk of at least one of cardiac inflammation, heart failure, an arrhythmia, or a stroke.

Example 3: The method of any of examples 1 or 2, wherein applying the machine learning model to the at least one extracted feature to produce data indicative of the risk of the cardiovascular event comprises applying the machine learning model to the at least one extracted feature to produce data indicative of a risk of hospitalization due to the cardiovascular event.

Example 4: The method of any of examples 1 through 3, wherein the amount of time within a pre-determined glucose level range comprises an amount of time corresponding to a portion of the continuous glucose sensor measurements in a first glucose range or a second glucose range.

Example 5: The method of any of examples 1 through 4, wherein the one or more statistical metrics comprise at least one of a standard deviation, a coefficient of variation, an average, a median, an interquartile range, or a maximum rate of change of at least one dataset of the continuous glucose sensor measurements, wherein the at least one dataset comprises different time intervals of the continuous glucose sensor measurements.

Example 6: The method of any of examples 1 through 5, wherein applying the machine learning model comprises determining that the amount of time in the pre-determined glucose level range is less than a first threshold or the number of hyperglycemic events is greater than a second threshold.

Example 7: The method of any of examples 1 through 6, wherein applying the machine learning model comprises determining that the amount of time in the pre-determined glucose level range is greater than or equal to a first threshold, the number of hyperglycemic events is less than or equal to a second threshold, and at least one of a standard deviation of a dataset of the continuous glucose sensor measurements is a greater than a third threshold, the number of hypoglycemic events is greater than a fourth threshold, or the amount of time in the pre-determined glucose level range is greater than a fifth threshold.

Example 8: The method of any of examples 1 through 7, wherein applying the machine learning model comprises computing a likelihood probability of a glucose level of the patient causing the cardiovascular event, wherein the likelihood probability is incorporated into the machine learning model by at least one of including the likelihood probability in the at least one feature, including the likelihood probability as an independent prior probability, or adjusting at least one prior probability for the cardiovascular event.

Example 9: The method of any of examples 1 through 8, wherein the output comprises a first output, and wherein generating the output further comprises generating a second output indicative of the risk of the cardiovascular event based on the first output and data corresponding to at least one of impedance or cardiac electrogram metrics.

Example 10: The method of any of examples 1 through 9, wherein extracting at least one feature further comprises extracting at least one second feature from data corresponding to at least one of impedance or cardiac electrogram metrics, wherein the at least one second feature comprises at least one of impedance, respiratory rate, night heart rate, heart rate variability, activity, or atrial fibrillation (AF) parameters.

Example 11: A method comprising: extracting at least one feature from continuous glucose sensor measurements of a patient over at least one time period, wherein the at least one feature comprises one or more of an amount of time within a pre-determined glucose level range, a number of hypoglycemia events, a number of hyperglycemia events, or one or more statistical metrics corresponding to the continuous glucose sensor measurements; applying a machine learning model to the at least one extracted feature to produce data indicative of a risk of a cardio-neurogenic event; and generating an output based on the risk of the risk of a cardio-neurogenic event.

Example 12: The method of example 11, wherein the cardio-neurogenic event comprises at least one of an ischemic stroke or a hemorrhagic stroke.

Example 13: The method of any of examples 11 or 12, wherein applying the machine learning model to the at least one extracted feature to produce data indicative of the risk of the cardiovascular event comprises applying the machine learning model to the at least one extracted feature to produce data indicative of a risk of hospitalization due to the cardiovascular event.

Example 14: A medical system comprising: processing circuitry communicably coupled to a glucose sensor and configured to generate continuous glucose sensor measurements of a patient, wherein the processing circuitry is further configured to: extract at least one feature from the continuous glucose sensor measurements over at least one time period, wherein the at least one feature comprises one or more of an amount of time within a pre-determined glucose level range, a number of hypoglycemia events, a number of hyperglycemia events, or one or more statistical metrics corresponding to the continuous glucose sensor measurements; apply a machine learning model to the at least one extracted feature to produce data indicative of a risk of a cardiovascular event; and generate output data based on the risk of the cardiovascular event.

Example 15: The medical system of example 14, wherein one or more of a glucose monitor, a cardiac monitor, a neuro monitor, or a computing device in communication with at least one of the glucose monitor or the cardiac monitor comprising the processing circuitry.

Example 16: The medical system of any of examples 14 or 15, wherein the cardiac monitor or the glucose monitor comprises the glucose sensor, wherein the cardiac monitor or the neuro monitor is a wearable or an implant.

Example 17: The medical system of any of examples 14 through 16, wherein to apply the machine learning model, the processing circuitry is further configured to apply the machine learning model to the at least one extracted feature to produce data indicative of a risk of at least one of cardiac inflammation, heart failure, an arrhythmia, or a stroke.

Example 18: The medical system of any of examples 14 through 17, wherein to apply the machine learning model, the processing circuitry is configured to: compute a likelihood probability that a glucose level of the patient causes the cardiovascular event; and incorporate the likelihood probability into the machine learning model by at least one of including the likelihood probability in the at least one feature, including the likelihood probability as an independent prior probability, or adjusting at least one prior probability for the cardiovascular event.

Example 19: The medical system of any of examples 14 through 18, wherein to apply the machine learning model, the processing circuitry is configured to: apply the machine learning model to the at least one extracted feature to produce data indicative of a risk of hospitalization due to the cardiovascular event.

Example 20: The medical system of any of examples 14 through 19, wherein the amount of time within a pre-determined glucose level range comprises an amount of time corresponding to a portion of the continuous glucose sensor measurements in a first glucose range or a second glucose range, wherein the one or more statistical metrics comprise at least one of a standard deviation, a coefficient of variation, an average, a median, an interquartile range, or a maximum rate of change of at least one dataset of the continuous glucose sensor measurements, wherein the at least one dataset comprises different time intervals of the continuous glucose sensor measurements.

Example 21: The medical system of any of examples 14 through 20, wherein to apply the machine learning model, the processing circuitry is configured to: determine that the amount of time in the pre-determined glucose level range is less than a first threshold or the number of hyperglycemic events is greater than a second threshold.

Example 22: The medical system of any of examples 14 through 21, wherein to apply the machine learning model, the processing circuitry is configured to: determine that the amount of time in the pre-determined glucose level range is greater than or equal to a first threshold, the number of hyperglycemic events is less than or equal to a second threshold, and at least one of a standard deviation of a dataset of the continuous glucose sensor measurements is a greater than a third threshold, the number of hypoglycemic events is greater than a fourth threshold, or the amount of time in the pre-determined glucose level range is greater than a fifth threshold.

Example 23: The medical system of any of examples 14 through 22, wherein the output data comprises first output data, and wherein to generate the output data, the processing circuitry is configured to: generate second output data indicative of the risk of the cardiovascular event based on the first output data and data corresponding to at least one of impedance or cardiac electrogram metrics.

Example 24: The medical system of any of examples 14 through 23, wherein the at least one feature comprises at least one first feature, and wherein to extract the at least one feature, the processing circuitry is configured to: extract at least one second feature from data corresponding to at least one of impedance or cardiac electrogram metrics, wherein the at least one second feature comprises at least one of impedance, respiratory rate, night heart rate, heart rate variability, activity, or atrial fibrillation (AF) parameters.

What is claimed is:

1. A method comprising:
   extracting at least one feature from continuous glucose sensor measurements of a patient over at least one time period, wherein the at least one feature comprises one or more of an amount of time within a pre-determined glucose level range, a number of hypoglycemia events, or a number of hyperglycemia events;
   applying a machine learning model to the at least one extracted feature to produce data indicative of a risk of a cardiovascular event; and
   generating an output based on the risk of the cardiovascular event.

2. The method of claim 1, wherein applying the machine learning model to the at least one extracted feature to produce data indicative of a risk of a cardiovascular event comprises applying the machine learning model to the at least one extracted feature to produce data indicative of a risk of at least one of cardiac inflammation, heart failure, an arrhythmia, or a stroke.

3. The method of claim 1, wherein applying the machine learning model to the at least one extracted feature to produce data indicative of the risk of the cardiovascular event comprises applying the machine learning model to the at least one extracted feature to produce data indicative of a risk of hospitalization due to the cardiovascular event.

4. The method of claim 1, wherein the amount of time within a pre-determined glucose level range comprises an amount of time corresponding to a portion of the continuous glucose sensor measurements in a first glucose range or a second glucose range.

5. The method of claim 1, wherein the at least one feature further comprises at least one of a standard deviation, a coefficient of variation, an average, a median, an interquartile range, or a maximum rate of change of at least one dataset of the continuous glucose sensor measurements, wherein the at least one dataset comprises different time intervals of the continuous glucose sensor measurements.

6. The method of claim 1, wherein the at least one feature comprises: the amount of time in the pre-determined glucose level range that is less than a first threshold or the number of hyperglycemic events that is greater than a second threshold.

7. The method of claim 1, wherein the at least one feature comprises:
the amount of time in the pre-determined glucose level range that is greater than or equal to a first threshold,
the number of hyperglycemic events that is less than or equal to a second threshold, and
at least one of a standard deviation of a dataset of the continuous glucose sensor measurements that is a greater than a third threshold, the number of hypoglycemic events that is greater than a fourth threshold, or the amount of time in the pre-determined glucose level range that is greater than a fifth threshold.

8. The method of claim 1, wherein applying the machine learning model comprises computing a likelihood probability of a glucose level of the patient causing the cardiovascular event, wherein the likelihood probability is incorporated into the machine learning model by at least one of including the likelihood probability in the at least one feature, including the likelihood probability as an independent prior probability, or adjusting at least one prior probability for the cardiovascular event.

9. The method of claim 1, wherein the output comprises a first output, and wherein generating the output further comprises generating a second output indicative of the risk of the cardiovascular event based on the first output and data corresponding to at least one of impedance or cardiac electrogram metrics.

10. The method of claim 1, wherein extracting at least one feature further comprises extracting at least one second feature from data corresponding to at least one of impedance or cardiac electrogram metrics, wherein the at least one second feature comprises at least one of impedance, respiratory rate, night heart rate, heart rate variability, activity, or atrial fibrillation (AF) parameters.

11. A method comprising:
extracting at least one feature from continuous glucose sensor measurements of a patient over at least one time period, wherein the at least one feature comprises one or more of an amount of time within a pre-determined glucose level range, a number of hypoglycemia events, a number of hyperglycemia events, or one or more statistical metrics corresponding to the continuous glucose sensor measurements;
applying a machine learning model to the at least one extracted feature to produce data indicative of a risk of a cardio-neurogenic event; and
generating an output based on the risk of a cardio-neurogenic event.

12. The method of claim 11, wherein the cardio-neurogenic event comprises at least one of an ischemic stroke or a hemorrhagic stroke.

13. The method of claim 11, wherein applying the machine learning model to the at least one extracted feature to produce data indicative of the risk of the cardio-neurogenic event comprises applying the machine learning model to the at least one extracted feature to produce data indicative of a risk of hospitalization due to the cardio-neurogenic event.

14. A medical system comprising:
processing circuitry communicably coupled to a glucose sensor and configured to generate continuous glucose sensor measurements of a patient, wherein the processing circuitry is further configured to:
extract at least one feature from the continuous glucose sensor measurements over at least one time period, wherein the at least one feature comprises one or more of an amount of time within a pre-determined glucose level range, a number of hypoglycemia events, or a number of hyperglycemia events;
apply a machine learning model to the at least one extracted feature to produce data indicative of a risk of a cardiovascular event; and
generate output data based on the risk of the cardiovascular event.

15. The medical system of claim 14, wherein one or more of a glucose monitor, a cardiac monitor, a neuro monitor, or a computing device in communication with at least one of the glucose monitor or the cardiac monitor comprises the processing circuitry.

16. The medical system of claim 15, wherein the cardiac monitor or the glucose monitor comprises the glucose sensor, wherein the cardiac monitor or the neuro monitor is a wearable or an implant.

17. The medical system of claim 14, wherein to apply the machine learning model, the processing circuitry is further configured to apply the machine learning model to the at least one extracted feature to produce data indicative of a risk of at least one of cardiac inflammation, heart failure, an arrhythmia, or a stroke.

18. The medical system of claim 14, wherein to apply the machine learning model, the processing circuitry is configured to:
compute a likelihood probability that a glucose level of the patient causes the cardiovascular event; and
incorporate the likelihood probability into the machine learning model by at least one of including the likelihood probability in the at least one feature, including the likelihood probability as an independent prior probability, or adjusting at least one prior probability for the cardiovascular event.

19. The medical system of claim 14, wherein to apply the machine learning model, the processing circuitry is configured to:
apply the machine learning model to the at least one extracted feature to produce data indicative of a risk of hospitalization due to the cardiovascular event.

20. The medical system of claim 14, wherein the amount of time within a pre-determined glucose level range comprises an amount of time corresponding to a portion of the continuous glucose sensor measurements in a first glucose range or a second glucose range,
wherein the at least one feature further comprises at least one of a standard deviation, a coefficient of variation, an average, a median, an interquartile range, or a maximum rate of change of at least one dataset of the continuous glucose sensor measurements, wherein the at least one dataset comprises different time intervals of the continuous glucose sensor measurements.

21. The medical system of claim 14, wherein the at least one feature further comprises:
the amount of time in the pre-determined glucose level range that is less than a first threshold or the number of hyperglycemic events that is greater than a second threshold.

22. The medical system of claim 14, wherein the at least one feature comprises:
the amount of time in the pre-determined glucose level range that is greater than or equal to a first threshold,
the number of hyperglycemic events that is less than or equal to a second threshold, and
at least one of a standard deviation of a dataset of the continuous glucose sensor measurements that is a greater than a third threshold, the number of hypoglycemic events that is greater than a fourth threshold, or the amount of time in the pre-determined glucose level range that is greater than a fifth threshold.

23. The medical system of claim 14, wherein the output data comprises first output data, and wherein to generate the output data, the processing circuitry is configured to:
generate second output data indicative of the risk of the cardiovascular event based on the first output data and data corresponding to at least one of impedance or cardiac electrogram metrics.

24. The medical system of claim 14, wherein the at least one feature comprises at least one first feature, and wherein to extract the at least one feature, the processing circuitry is configured to:
extract at least one second feature from data corresponding to at least one of impedance or cardiac electrogram metrics, wherein the at least one second feature comprises at least one of impedance, respiratory rate, night heart rate, heart rate variability, activity, or atrial fibrillation (AF) parameters.

* * * * *